United States Patent
MacEwan et al.

(10) Patent No.: US 12,263,269 B2
(45) Date of Patent: Apr. 1, 2025

(54) PARTICLE-FORM HYBRID-SCALE FIBER MATRIX

(71) Applicant: Acera Surgical, Inc., St. Louis, MO (US)

(72) Inventors: Matthew R. MacEwan, St. Louis, MO (US); Lily Jeng, St. Louis, MO (US); Abdolrasol Rahimi, St. Louis, MO (US); Manisha Jassal, St. Louis, MO (US); Tamas Kovacs, St. Louis, MO (US)

(73) Assignee: Acera Surgical, Inc., St. Louis, MO (US)

( * ) Notice: Subject to any disclaimer, the term of this patent is extended or adjusted under 35 U.S.C. 154(b) by 0 days.

(21) Appl. No.: 17/877,485

(22) Filed: Jul. 29, 2022

(65) Prior Publication Data

US 2023/0033599 A1    Feb. 2, 2023

Related U.S. Application Data

(60) Provisional application No. 63/203,737, filed on Jul. 29, 2021.

(51) Int. Cl.
*A61L 26/00* (2006.01)

(52) U.S. Cl.
CPC .......... *A61L 26/0052* (2013.01); *A61L 26/008* (2013.01); *A61L 2400/06* (2013.01); *A61L 2430/34* (2013.01)

(58) Field of Classification Search
None
See application file for complete search history.

(56) References Cited

U.S. PATENT DOCUMENTS

| | | |
|---|---|---|
| 2,068,703 A | 1/1937 | Powdermaker |
| 3,280,229 A | 10/1966 | Simons |
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,692,618 A | 9/1972 | Dorschner et al. |
| 3,740,302 A | 6/1973 | Soehngen |
| 3,802,817 A | 4/1974 | Matsuki |
| 3,849,241 A | 11/1974 | Butin et al. |
| 3,909,009 A | 9/1975 | Cvetko et al. |
| 4,044,404 A | 8/1977 | Martin et al. |
| 4,340,563 A | 7/1982 | Appel et al. |
| 4,468,428 A | 8/1984 | Early et al. |
| 4,738,740 A | 4/1988 | Pinchuk et al. |
| 4,965,110 A | 10/1990 | Berry |
| 5,024,789 A | 6/1991 | Berry |
| 5,079,080 A | 1/1992 | Schwarz |
| 5,306,550 A | 4/1994 | Nishiyama et al. |
| 5,464,450 A | 11/1995 | Buscemi et al. |
| 5,591,335 A | 1/1997 | Barboza et al. |
| 5,626,611 A | 5/1997 | Liu et al. |
| 5,634,944 A | 6/1997 | Magram |
| 5,795,584 A | 8/1998 | Totakura et al. |
| 5,851,937 A | 12/1998 | Wu et al. |
| 5,997,568 A | 12/1999 | Liu |
| 6,147,135 A | 11/2000 | Yuan et al. |
| 6,162,535 A | 12/2000 | Turkevich et al. |
| 6,171,338 B1 | 1/2001 | Talja et al. |
| 6,180,848 B1 | 1/2001 | Flament et al. |
| 6,183,670 B1 | 2/2001 | Torobin et al. |
| 6,265,333 B1 | 7/2001 | Dzenis et al. |
| 6,306,424 B1 | 10/2001 | Vyakarnam et al. |
| 6,391,060 B1 | 5/2002 | Ory et al. |
| 6,596,296 B1 | 7/2003 | Nelson et al. |
| 6,630,231 B2 | 10/2003 | Perez et al. |
| 6,649,807 B2 | 11/2003 | Mizutani |
| 6,685,956 B2 | 2/2004 | Chu et al. |
| 6,689,374 B2 | 2/2004 | Chu et al. |
| 6,713,011 B2 | 3/2004 | Chu et al. |
| 6,753,454 B1 | 6/2004 | Smith et al. |
| 6,790,455 B2 | 9/2004 | Chu et al. |
| 6,797,655 B2 | 9/2004 | Rudisill |
| 6,946,506 B2 | 9/2005 | Bond et al. |
| 7,134,857 B2 | 11/2006 | Andrady et al. |
| 7,172,765 B2 | 2/2007 | Chu et al. |
| 7,192,604 B2 | 3/2007 | Brown et al. |
| 7,655,070 B1 | 2/2010 | Dallas et al. |

(Continued)

FOREIGN PATENT DOCUMENTS

| | | |
|---|---|---|
| AU | 2011268321 | 1/2013 |
| AU | 2012390291 | 9/2017 |

(Continued)

OTHER PUBLICATIONS

Herron, Treatment of a Complex Pressure Ulcer Using a Synthetic Hybrid-Scale Fiber Matrix, Apr. 16, 2021, Cureus, vol. 14 iss. 4, pp. 1-4. (Year: 2021).*
Boda et al., Electrospraying Electrospun Nanofiber Segments into InjectableMicrospheres for Potential Cell Delivery, Jul. 11, 2018, ACS Applied Materials & Interfaces, vol. 10, pp. 25069-25079. (Year: 2018).*
U.S. Appl. No. 62/154,286, filed Apr. 29, 2015, Johnson.
3rd International Conference on Electrospinning Conference Program dated Aug. 4-7, 2004, www.ceramics.org/electrospin2014.
ASTM International, "Standard Guide for Assessing Microstructure of Polymeric Scaffolds for Use in Tissue-Engineered Medical Products" dated Mar. 27, 2013.

(Continued)

*Primary Examiner* — Brian J Davis
(74) *Attorney, Agent, or Firm* — Knobbe, Martens, Olson & Bear, LLP

(57) ABSTRACT

Particles of non-woven graft materials for use in specialized surgical procedures such as soft tissue repair and wound management procedures, methods for making the powder, and methods for repairing tissue such as neurological tissue using the powder are disclosed. The particles can advantageously be used to fill irregular shaped areas or can be used in conjunction with non-woven graft materials.

13 Claims, 6 Drawing Sheets

(56) References Cited

U.S. PATENT DOCUMENTS

| | | |
|---|---|---|
| 7,759,082 B2 | 7/2010 | Bowlin et al. |
| 7,799,262 B1 | 9/2010 | Kim |
| 7,846,466 B2 | 12/2010 | Shea et al. |
| 7,879,093 B2 | 2/2011 | Wei et al. |
| 7,981,353 B2 | 7/2011 | Mitchell et al. |
| 8,066,932 B2 | 11/2011 | Xu |
| 8,222,166 B2 | 7/2012 | Chu et al. |
| 8,273,369 B2 | 9/2012 | Moloye-Olabisi |
| 8,652,215 B2 | 2/2014 | Bellamkonda et al. |
| 8,728,463 B2 | 5/2014 | Atala et al. |
| 8,728,817 B2 | 5/2014 | Ogle et al. |
| 8,809,212 B1 | 8/2014 | Dirk et al. |
| 8,852,621 B2 | 10/2014 | Patel |
| 9,074,172 B2 | 7/2015 | Johnson |
| 9,085,830 B2 | 7/2015 | Mitchell et al. |
| 9,163,331 B2 | 10/2015 | Atala et al. |
| 9,168,231 B2 | 10/2015 | Patel et al. |
| 9,345,486 B2 | 5/2016 | Zhang et al. |
| 9,393,097 B2 | 7/2016 | McCullen et al. |
| 9,476,026 B2 | 10/2016 | Arinzeh et al. |
| 9,487,893 B2 | 11/2016 | Moore et al. |
| 9,539,365 B2 | 1/2017 | Kasunga et al. |
| 9,572,909 B2 | 2/2017 | Simpson et al. |
| 9,585,666 B2 | 3/2017 | Yu et al. |
| 9,737,632 B2 | 8/2017 | Johnson et al. |
| 9,884,027 B2 | 2/2018 | Johnson |
| 9,938,373 B2 | 4/2018 | Wang et al. |
| 10,016,464 B2 | 7/2018 | Murphy et al. |
| 10,080,687 B2 | 9/2018 | MacEwan |
| 10,124,089 B2 | 11/2018 | MacEwan |
| 10,149,749 B2 | 12/2018 | MacEwan et al. |
| 10,166,315 B2 | 1/2019 | Johnson et al. |
| 10,227,568 B2 | 3/2019 | Johnson |
| 10,231,821 B2 | 3/2019 | Gabriele et al. |
| 10,233,427 B2 | 3/2019 | Johnson |
| 10,239,262 B2 | 3/2019 | Johnson |
| 10,294,449 B2 | 5/2019 | Johnson |
| 10,335,154 B2 | 7/2019 | Johnson et al. |
| 10,363,041 B2 | 7/2019 | Yu et al. |
| 10,381,672 B2 | 8/2019 | Lee et al. |
| 10,405,963 B2 | 9/2019 | McAlpine et al. |
| 10,406,346 B2 | 9/2019 | Scott-Carnell et al. |
| 10,413,574 B2 | 9/2019 | Fong et al. |
| 10,420,856 B2 | 9/2019 | Arinzeh et al. |
| 10,441,403 B1 | 10/2019 | MacEwan et al. |
| 10,441,685 B2 | 10/2019 | MacEwan |
| 10,588,734 B2 | 3/2020 | MacEwan et al. |
| 10,617,512 B2 | 4/2020 | MacEwan |
| 10,632,228 B2 | 4/2020 | MacEwan |
| 10,682,444 B2 | 6/2020 | MacEwan |
| 10,738,152 B2 | 8/2020 | Wang et al. |
| 10,888,409 B2 | 1/2021 | MacEwan |
| 11,000,358 B2 | 5/2021 | MacEwan |
| 11,096,772 B1 | 8/2021 | MacEwan et al. |
| 11,176,234 B2 | 11/2021 | MacEwan et al. |
| 11,224,677 B2 | 1/2022 | MacEwan |
| 11,826,487 B2 | 11/2023 | MacEwan |
| 2002/0081732 A1 | 6/2002 | Bowlin et al. |
| 2002/0090725 A1 | 7/2002 | Simpson et al. |
| 2002/0173213 A1 | 11/2002 | Chu et al. |
| 2002/0192251 A1 | 12/2002 | Collin |
| 2003/0004579 A1 | 1/2003 | Rousseau et al. |
| 2003/0054035 A1 | 3/2003 | Chu et al. |
| 2004/0013819 A1 | 1/2004 | Hou et al. |
| 2004/0018226 A1 | 1/2004 | Wnek et al. |
| 2004/0037813 A1 | 2/2004 | Simpson et al. |
| 2004/0096532 A1 | 5/2004 | Dubson et al. |
| 2004/0102614 A1 | 5/2004 | Islam et al. |
| 2005/0104258 A1 | 5/2005 | Lennhoff |
| 2005/0167311 A1 | 8/2005 | Tonsfeldt et al. |
| 2005/0222591 A1 | 10/2005 | Gingras et al. |
| 2006/0014460 A1 | 1/2006 | Alexander Isele et al. |
| 2006/0085063 A1 | 4/2006 | Shastri et al. |
| 2006/0094320 A1 | 5/2006 | Chen et al. |
| 2006/0153904 A1 | 7/2006 | Smith et al. |
| 2006/0193578 A1 | 8/2006 | Ouderkirk et al. |
| 2006/0204539 A1 | 9/2006 | Atala et al. |
| 2006/0240110 A1 | 10/2006 | Kiick et al. |
| 2006/0246798 A1 | 11/2006 | Reneker et al. |
| 2006/0263417 A1 | 11/2006 | Lelkes et al. |
| 2006/0264140 A1 | 11/2006 | Andrady |
| 2007/0073344 A1 | 3/2007 | Jahns et al. |
| 2007/0152378 A1 | 7/2007 | Kim |
| 2007/0155273 A1 | 7/2007 | Chu et al. |
| 2007/0225631 A1 | 9/2007 | Bowlin et al. |
| 2007/0269481 A1 | 11/2007 | Li et al. |
| 2008/0065123 A1 | 3/2008 | Yli-Urpo et al. |
| 2008/0112998 A1 | 5/2008 | Wang |
| 2008/0207798 A1 | 8/2008 | Hellring et al. |
| 2008/0208358 A1 | 8/2008 | Bellamkoda et al. |
| 2008/0220042 A1 | 9/2008 | Hashi et al. |
| 2008/0237934 A1 | 10/2008 | Reneker et al. |
| 2009/0028921 A1 | 1/2009 | Arinzeh |
| 2009/0074832 A1 | 3/2009 | Zussman et al. |
| 2009/0075354 A1 | 3/2009 | Reneker et al. |
| 2009/0155326 A1 | 6/2009 | Mack et al. |
| 2009/0162468 A1 | 6/2009 | Barinov et al. |
| 2009/0171467 A1 | 7/2009 | Mann et al. |
| 2009/0202616 A1 | 8/2009 | Chong et al. |
| 2009/0214614 A1 | 8/2009 | Everland et al. |
| 2009/0228021 A1 | 9/2009 | Leung |
| 2009/0317446 A1 | 12/2009 | Tan et al. |
| 2010/0003305 A1 | 1/2010 | Pattanaik |
| 2010/0047309 A1 | 2/2010 | Lu et al. |
| 2010/0061962 A1 | 3/2010 | Li |
| 2010/0076377 A1 | 3/2010 | Ehrenreich et al. |
| 2010/0092687 A1 | 4/2010 | Sumida et al. |
| 2010/0093093 A1 | 4/2010 | Leong et al. |
| 2010/0119564 A1 | 5/2010 | Kasuga et al. |
| 2010/0120115 A1 | 5/2010 | Ogle et al. |
| 2010/0137902 A1 | 6/2010 | Lee et al. |
| 2010/0166854 A1 | 7/2010 | Michniak-Kohn et al. |
| 2010/0174368 A1 | 7/2010 | Lynch et al. |
| 2010/0179659 A1 | 7/2010 | Li et al. |
| 2010/0185219 A1 | 7/2010 | Gertzman et al. |
| 2010/0190254 A1 | 7/2010 | Chian et al. |
| 2010/0233115 A1 | 9/2010 | Patel et al. |
| 2010/0273258 A1 | 10/2010 | Lannutti et al. |
| 2010/0291182 A1 | 11/2010 | Palasis et al. |
| 2010/0292791 A1 | 11/2010 | Lu et al. |
| 2010/0297208 A1 | 11/2010 | Fry et al. |
| 2010/0330419 A1 | 12/2010 | Cui et al. |
| 2010/0331980 A1 | 12/2010 | Lee et al. |
| 2011/0014289 A1 | 1/2011 | Datta et al. |
| 2011/0087277 A1 | 4/2011 | Viola et al. |
| 2011/0098826 A1 | 4/2011 | Mauck et al. |
| 2011/0101571 A1 | 5/2011 | Reneker |
| 2011/0111012 A1 | 5/2011 | Pepper et al. |
| 2011/0150973 A1 | 6/2011 | Bowlin et al. |
| 2011/0152897 A1 | 6/2011 | Bates |
| 2011/0174158 A1 | 7/2011 | Walls et al. |
| 2011/0180951 A1 | 7/2011 | Teo et al. |
| 2011/0242310 A1 | 10/2011 | Beebe, Jr. et al. |
| 2011/0280919 A1 | 11/2011 | Moloye-Olabisi et al. |
| 2011/0287082 A1 | 11/2011 | Smith et al. |
| 2012/0015331 A1 | 1/2012 | Wood et al. |
| 2012/0029654 A1 | 2/2012 | Xu et al. |
| 2012/0040581 A1 | 2/2012 | Kim |
| 2012/0123342 A1 | 5/2012 | Andrews et al. |
| 2012/0165957 A1 | 6/2012 | Everland et al. |
| 2012/0221025 A1 | 8/2012 | Simpson et al. |
| 2012/0225039 A1 | 9/2012 | Li et al. |
| 2012/0265300 A1 | 10/2012 | Mauck et al. |
| 2012/0310260 A1 | 12/2012 | Hamlin et al. |
| 2012/0330437 A1 | 12/2012 | El-Kurdi et al. |
| 2013/0030548 A1 | 1/2013 | Ling |
| 2013/0035704 A1 | 2/2013 | Dudai |
| 2013/0110138 A1 | 2/2013 | Hurtado et al. |
| 2013/0115457 A1 | 5/2013 | Haynie et al. |
| 2013/0144249 A1 | 6/2013 | Fenton et al. |
| 2013/0197663 A1 | 8/2013 | MacEwan et al. |
| 2013/0251762 A1 | 9/2013 | Wei et al. |
| 2013/0338791 A1 | 12/2013 | McCullen et al. |
| 2014/0030315 A1 | 1/2014 | Johnson |

(56) References Cited

U.S. PATENT DOCUMENTS

| | | |
|---|---|---|
| 2014/0081297 A1 | 3/2014 | Hoke et al. |
| 2014/0128345 A1 | 5/2014 | Woodrow et al. |
| 2014/0272225 A1 | 9/2014 | Johnson |
| 2014/0288663 A1 | 9/2014 | Borden et al. |
| 2014/0303727 A1 | 10/2014 | Atlas et al. |
| 2014/0322512 A1 | 10/2014 | Pham et al. |
| 2015/0045818 A1 | 2/2015 | Kim et al. |
| 2015/0132423 A1 | 5/2015 | Johnson |
| 2015/0133454 A1 | 5/2015 | Choy et al. |
| 2015/0190285 A1 | 7/2015 | MacEwan |
| 2015/0250927 A1 | 9/2015 | MacEwan |
| 2015/0297791 A1 | 10/2015 | Patel et al. |
| 2015/0342719 A1 | 12/2015 | Chen et al. |
| 2016/0022873 A1 | 1/2016 | Besner et al. |
| 2016/0083692 A1 | 3/2016 | Hardy et al. |
| 2016/0083868 A1 | 3/2016 | Park |
| 2016/0136330 A1 | 5/2016 | Benkirane-Jessel et al. |
| 2016/0302869 A1 | 10/2016 | Chopra |
| 2016/0317706 A1 | 11/2016 | Johnson |
| 2017/0095591 A1 | 4/2017 | Zuhaib et al. |
| 2017/0119886 A1 | 5/2017 | Johnson et al. |
| 2017/0182206 A1 | 6/2017 | Johnson et al. |
| 2017/0182211 A1 | 6/2017 | Raxworthy et al. |
| 2017/0319323 A1 | 11/2017 | MacEwan |
| 2017/0319742 A1 | 11/2017 | Johnson et al. |
| 2018/0116973 A1 | 5/2018 | Johnson |
| 2018/0161185 A1 | 6/2018 | Kresslein et al. |
| 2018/0174367 A1 | 6/2018 | Marom et al. |
| 2018/0221537 A1 | 8/2018 | Johnson et al. |
| 2018/0237952 A1 | 8/2018 | Johnson et al. |
| 2018/0245243 A1 | 8/2018 | Krieger et al. |
| 2018/0263919 A1 | 9/2018 | Hoke et al. |
| 2018/0368917 A1 | 12/2018 | Dekel et al. |
| 2019/0015563 A1 | 1/2019 | MacEwan |
| 2019/0021837 A1 | 1/2019 | MacEwan et al. |
| 2019/0054036 A1 | 2/2019 | Johnson et al. |
| 2019/0102880 A1 | 4/2019 | Parpara et al. |
| 2019/0105128 A1 | 4/2019 | Velazquez et al. |
| 2019/0134267 A1 | 5/2019 | Francis et al. |
| 2019/0134570 A1 | 5/2019 | Pintauro et al. |
| 2019/0153398 A1 | 5/2019 | Johnson |
| 2019/0249127 A1 | 5/2019 | Johnson |
| 2019/0175786 A1 | 6/2019 | Cohen et al. |
| 2019/0269829 A1 | 9/2019 | Johnson et al. |
| 2019/0271098 A1 | 9/2019 | Johnson et al. |
| 2019/0282351 A1 | 9/2019 | Mathisen et al. |
| 2019/0328393 A1 | 10/2019 | Yu et al. |
| 2019/0330419 A1 | 10/2019 | Song et al. |
| 2019/0350688 A1 | 11/2019 | Hurtado et al. |
| 2019/0365520 A1 | 12/2019 | MacEwan |
| 2019/0365958 A1 | 12/2019 | MacEwan |
| 2019/0374227 A1 | 12/2019 | Johnson et al. |
| 2020/0000570 A1 | 1/2020 | MacEwan et al. |
| 2020/0046883 A1 | 2/2020 | Martin et al. |
| 2020/0060800 A1 | 2/2020 | MacEwan et al. |
| 2020/0197153 A1 | 6/2020 | MacEwan et al. |
| 2020/0229679 A1 | 7/2020 | Zhao et al. |
| 2020/0242767 A1 | 7/2020 | Zhao et al. |
| 2020/0277711 A1 | 9/2020 | Xie |
| 2021/0001014 A1 | 1/2021 | MacEwan |
| 2021/0030525 A1 | 2/2021 | MacEwan et al. |
| 2021/0052362 A1 | 2/2021 | MacEwan et al. |
| 2021/0128792 A1 | 5/2021 | Dunbar et al. |
| 2021/0228782 A1 | 7/2021 | MacEwan |
| 2021/0267746 A1 | 9/2021 | MacEwan et al. |
| 2021/0338408 A1 | 11/2021 | MacEwan et al. |
| 2023/0030107 A1 | 2/2023 | MacEwan et al. |
| 2023/0074964 A1 | 3/2023 | MacEwan et al. |

FOREIGN PATENT DOCUMENTS

| | | |
|---|---|---|
| CA | 2094908 C | 2/2000 |
| CA | 2386810 C | 9/2013 |
| CA | 2802482 | 6/2017 |
| CN | 102260963 | 11/2011 |
| CN | 102691176 | 9/2012 |
| CN | 103599562 | 2/2014 |
| CN | 104894750 | 9/2015 |
| DE | 102014107826 A1 | 12/2014 |
| EP | 0314109 | 5/1989 |
| EP | 0515522 B1 | 10/1993 |
| EP | 0571415 | 7/1995 |
| EP | 0757127 | 2/1997 |
| EP | 2045375 | 3/2011 |
| EP | 2358301 | 8/2011 |
| EP | 2599858 | 6/2013 |
| EP | 2582868 | 3/2018 |
| EP | 2897561 | 4/2020 |
| EP | 3508641 | 8/2020 |
| EP | 3741896 | 11/2020 |
| GB | 1286858 | 8/1972 |
| GB | 2181207 | 4/1987 |
| GB | 2195251 | 4/1988 |
| JP | H03161563 | 7/1991 |
| JP | 3487722 B2 | 1/2004 |
| JP | 2005-534828 | 11/2005 |
| JP | 2006-283241 | 10/2006 |
| JP | 2006-328562 | 12/2006 |
| JP | 2007-303021 | 11/2007 |
| JP | 2008-223186 | 9/2008 |
| JP | 2009061109 | 3/2009 |
| JP | 2011-059786 | 3/2011 |
| JP | 2011-509786 | 3/2011 |
| JP | 4769871 | 9/2011 |
| JP | 4979264 | 7/2012 |
| JP | 2012-528464 | 11/2012 |
| JP | 2013-518996 | 5/2013 |
| JP | 2013-534979 | 9/2013 |
| JP | 6295258 | 3/2018 |
| JP | 6328672 | 5/2018 |
| KR | 100439871 B1 | 7/2004 |
| KR | 2006-0118937 | 11/2006 |
| KR | 10-2007-0047873 | 5/2007 |
| KR | 10-1703095 | 2/2017 |
| SG | 186379 | 1/2013 |
| SG | 11201502207 W | 4/2015 |
| WO | WO 1991/001695 | 2/1991 |
| WO | WO 01/27365 | 4/2001 |
| WO | WO 02/00149 | 1/2002 |
| WO | WO 2004/016839 | 2/2004 |
| WO | WO 2006/096791 | 9/2006 |
| WO | WO 2006/123858 | 11/2006 |
| WO | WO 2007/086910 | 8/2007 |
| WO | WO 2008/069760 | 6/2008 |
| WO | WO 2009/093023 | 7/2009 |
| WO | WO 2010/041944 | 4/2010 |
| WO | WO 2010/042651 | 4/2010 |
| WO | WO 2010/112564 | 10/2010 |
| WO | WO 2010/138619 | 12/2010 |
| WO | WO 2011/095141 | 8/2011 |
| WO | WO 2011/159889 | 12/2011 |
| WO | WO 2012/080706 | 6/2012 |
| WO | WO 2013/106822 | 1/2013 |
| WO | WO 2013/025819 | 2/2013 |
| WO | WO 2013/050428 | 4/2013 |
| WO | WO 2013/078051 | 5/2013 |
| WO | WO 2014/031721 | 2/2014 |
| WO | WO 2014046669 | 3/2014 |
| WO | WO 2014/145864 | 9/2014 |
| WO | WO 2014/152906 | 9/2014 |
| WO | WO 2015/048224 | 4/2015 |
| WO | WO 2015/116917 | 8/2015 |
| WO | WO 2015/153011 | 10/2015 |
| WO | WO 2015/157485 | 10/2015 |
| WO | WO 2016/176559 | 11/2016 |
| WO | WO 2017/024263 | 2/2017 |
| WO | WO 2017/035500 | 3/2017 |
| WO | WO 2017/044982 | 3/2017 |
| WO | WO 2017/079328 | 5/2017 |
| WO | WO 2017/196325 | 11/2017 |
| WO | WO 2018/112203 | 6/2018 |
| WO | WO 2018/144858 | 8/2018 |

(56) References Cited

FOREIGN PATENT DOCUMENTS

| WO | WO 2023/007443 | 2/2023 |
|----|----------------|--------|
| WO | WO 2023/007444 | 2/2023 |

OTHER PUBLICATIONS

Barbol T et al. Biocompalibility evaluation of dura maTer substitutes in an animal model. Neurological research2001; vol. 23 pp. 813-820.

Beachley V et al. "Polymer nanofibrous structures: Fabrication, biofunctionalization, and cell interactions." Prog Polym Sci. 2010;35(7) pp. 868-892.

Beheshtkhoo et al. "Fabrication and Properties of Collagen and Polyurethane Polymeric Nanofibers Using Electrospinning Techniques" Journal of Environmental Treatment Techniques 2019, vol. 7, Issue 4, pp. 802-807.

Bhattarai et al. "Electrospun chitosa-based nanofibers and their cellular compatibility", Biomaterials, vol. 26, Issue 31, Nov. 2005, pp. 6176-6184.

Bognitzki et al., "Nanostructured Fibers via Electrospinning", Advanced Mater. 2001, 13. No. 1, Jan. 5, pp. 70-72.

Bognitzki et al., "Preparation of Fibers with Nanoscaled Morphologies: Electrospinning of Polmer Blends" Polymer Enginering and Science, Jun. 2001, vol. 41, No. 6, pp. 982-989.

Boland et al., "Tailoring Tissue Engineering Scafforlds Using Elactrostatic Proceedings Techniques: A Study of Poly(Glycolic acid) Electrospinning," Journal of Macromolecular Science 38:1231-1243 (2001), doi: 10.1081/MA-100108380.

Camposeo et al., "Lobal Mechanical Properties of Electrospun Fibers Correlate to Their Internal Nanostructure" Nano Lett. 2013, pp. 13, 5056-5062.

Chen et al. "Electrospun 3D Fibrous Scaffolds for Chronic Wound Repair," 2016, Materials 9(272):1-12.

Chen, Rui, et al. "Preparation and characterization of coaxial electrospun thermoplastic polyurethane/collagen compound nanofibers for tissue engineering applications." Colloids and Surfaces B: Biointerfaces 79.2 (2010) pp. 315-325.

Chen, Rui, et al. "Preparation and Study of TPU/Collagen Complex Nanofiber via Electrospinning." AATCC review 10.2 (2010).

Cheng et al, "Engineering the Microstructure of Electrospun Fibrous Scaffolds by Microtopography," Biomacromolecules 14:1349-1360 (2013), doi: 10.1021/bm302000n).

Choi, Sung-Seen, et al. "Formation of interfiber bonding in electrospun poly (etherimide) nanofiber web." Journal of materials science 39.4 (2004) pp. 1511-1513.

Chong et al., "Evaluation of electrospun PCL/gelatin nanofibrous scaffold for wound healing and layered dermal reconstruction," Acta Biomaterialia 3:321-330 (2007) doi: 10.1016/j.actbio.2007.10.002 (2007).

Clark et al. "Investigation of the Effects of Cell Seeding on Neotissue Formation in a Tissue Engineered Trachea" J Pediatr Surg. Jan. 2016; 51(1) 49-55.

Cole et al. A comparative long-term assessment of four soft tissue substitutes. Aesthetic surgery journal I theAmerican Society for Aesthetic Plastic surgery 2011; vol. 31 pp. 674-681.

Cui et al., "Controlled assembly of poly(vinyl pyrrolidone) fibers through an electric-field-assisted electrospinning method," Applied Physics A, 103(1): 167-172 (2011).

Davis, et al., "A biodegradable compsite artifical tendon," Journal of Materials Science: Materials in Medicine 3,359-364 (1992).

Deitzel et al. "The effect of processing variables on the morphology of electrospun nanofibers and textiles" Polymer 42 (2001) pp. 261-272.

Dempsey et al., "Micropatterning of Electrospun Polyurethane Fibers Through Control of Surface Topography," Macromolecular Materials and Engineering 295: 990-994 (2020), doi: 10.1002/mame. 201000152.

Dhandayuthapani et al. "Polymeric Scaffolds in Tissue Engineering Application: A Review" 2011, International Journal of Polymer Science 2011, Article ID 290602, 19 pages.

Diaz et al., "Fabrication of structured micro and nanofibers by coaxial electrospinning," Journal of Physics, Conference Series 127: 1-8 (2008), goi: 10.1088/1742-6596/127/1/012008.

Ding et al., "Fabrication of blend biodegradeable nanofibrous nonwoven mats via multi-jet electrospinning," Polymer 45: 1895-1902 (2004), doi: 10.1016/j.polymer.2004.01.026.

Doshi, et al., "Electrospinning Process and Applications of Electrospun Fibers" 35 J. Electrostatics 151 (1995).

Dubsky et al., "Nanofibers prepared by needleless electrospinning technology as scaffolds for wound healing," J Mater Sci: Mater Med, DOI 10.1007/s 10856-012-4577-7, Feb. 2012.

Dzenis et al., "Hierarchical nano-/micromaterials based on electrospun polymer fibers: Predictive models for thermomechanical behavior" Journal of Computer-Aided Materials Design, pp. 3, 403-408 (1996).

Dzenis et al., "Polymer Hybrid Nano/Micro Composites," Proceedings of the American Society for Composites Ninth Technical Conference, pp. 657-665, 1994.

Fang et al. "Electrospinning: an advanced nanofiber production technology." In: H. Niu, H. Zhou and H. Wang (Eds.), Energy Harvesting Properties of Electrospun Nanofibers (1st ed. [online], pp. 1-1-1-44). IOP Publishing Ltd. (2020). https://iopscience.iop.org/book/978-0-7503-2005-4/chapter/bk978-0-7503-2005-4ch1 (Accessed Apr. 6, 2021), doi 10.1088/978-0-7503-2005-4ch1.

Figallo et al. "Micropatterned biopolymer 3D scaffold for static and dynamic culture of human fibroblasts" Biotechnol Prog. Jan.-Feb. 2007;23(1):210-6. doi: 10.1021/bp0602092.

Foy, et al., Allergic reaction to a bovine dural substitute following spinal cord untethering. Case report, Journal of Neurosurgery Pediatrics 2008; vol. 1, pp. 167-169.

Fridrikh, et al., "Controlling the Fiber Diameter during Electrospinning" The American Physical Society 2003; vol. 90, No. 14.

Gibson, et al., Electrospun Fiber Mais: Transport Properties, AlChE Journal, 1999, vol. 45, No. 1, pp. 190-195.

Gnavi et al., "The influence of electrospun fibre size on Schwann cell behaviour and axonal outgrowth." Mater Sci Eng C Mater Biol Appl. Mar. 2015;48:620-31.

Grafe et al., "Nanofiber Webs from Electrospinning," Nonwovens in Filtration—Fifth International Conference (2003).

Huang et al., "A review on polymer nanofibers by electrospinning and their applications in nanocomposites," Composites Science and Technology 63: 2223-2253 (2003), doi: 10.1016/S0266-3538(03)00178-7.

Huang, et al., "Generation of Synthetic Elastin-Mimetic Small Diameter Fibers and Fiber Networks", Macromolecules 2000, 33, 2989-2997.

Jaeger, et al. "Electrospinning of Ultra-Thin Polymer Fibers", Macromol. Symp. 127, 141-150 (1998).

Ju et al., "Bilayered scaffold for engineering cellularized blood vessels," Biomaterials 31: 4313-4321 (2010), doi: 10.1016/j.biomaterials.2010.02.002.

Kenawy et al., "Release of tetracycline hydrochloride from electrospun poly(ethylene-co-vinylacetate), poly(lactic acid), and a blend," Journal of Controlled Release 81: 57-64 (2002), doi: 10.1016/S0168-3659(02)00041-X.

Khil, et al., "Novel Fabricated Matrix Via Electrospinning for Tissue Engineering," Wiley Periodicals, Inc. 2004.

Kidoaki et al., "Mesoscopic spatial designs of nano- and microfiber meshes for tissue-engineering matrix and scaffold based on newly devised multilayering and mixing electrospinning techniques," Biomaterials 26: 37-46 (2005), doi: 10.1016/j.biomaterials.2004.01.063.

Kim et al., "Controlled design of aligned and random nanofibers for 3D bi-functionalized nerve conduits fabricated via a novel electrospinning set-up", Sci Rep vol. 6:23761 (2016).

Kumar et al., "Nanofibers: Effective Generation by Electrospinning and Their Applications," Journal of Nanoscience and Nanotechnology, vol. 12, 1-25, 2012.

Le et al., "Engineering a Biocompatible Scaffold with Either Micrometre or Nanometre Scale Surface Topography for Promoting Protein

(56) References Cited

OTHER PUBLICATIONS

Adsorption and Cellular Response," International Journal of Biomaterials 2013: 1-16 (2013), doi: 10.115/2013/782549.
Lee et al., "Development of a composite vascular scaffolding system that withstands physiological vascular conditions," Biomaterials 29: 2891-2898 (2008), doi: 10.1016/j.biomaterials.2008.03.032.
Li et al., "Direct Fabrication of Composite and Ceramic Hollow Nanofibers by Electrospinning" Nano Lett. 2004, 4, 933-938.
Li et al., "Electrospinning of Nanofibers: Reinventing the Wheel?" Adv. Mater. Nov. 2004, 16, 1151-1170.
Li, et al., "Electrospinning Nanofibers as Uniaxially Aligned Arrays and Layer-by-Layer Stacked Films" Adv. Mater. 2004, 16, 361-36.
Li, et al., "Electrospinning of Polymeric and Ceramic Nanofibers as 20 Uniaxially Aligned Arrays" Nano Lett. 2003, 3, 1167-1171.
Liu et al, "Electrospun Fibrous Mats on Lithographically Micropatterned Collectors to Control Cellular Behaviors," Langmuir 28:17134-17142 (2012), doi: 10.1021/la303490x).
Liu, L-Q et al. "Tensile mechanics of electrospun multiwalled nanotube/poly (methyl methacrylate) nanofibers." Advanced Materials 19.9 (2007) pp. 1228-1233.
MacEwan et al., "What makes the optimal wound healing material? A review of current science and introduction of a synthetic nanofabricated wound care scaffold", Cureus, vol. 9(10):1-12 (2017).
Madhugiri, S. et al., "Electrospun MEH-PPV/SBA-15 Composite Nanofibers Using a Dual Syringe Method," J. Am. Chem. Soc., 125: 14531-14538 (2003).
Manavitehrani et al. "Biomedical Applications of Biodegradable Polyesters" 2016, Polymers 8(20):1-32.
Martinez-Lage et al., "Accidental transmission of Creutzfeldt-Jakob disease by dural cadaveric grafts," Journal of Neurology, Neurosurgery & Psychiatry, 57(9): 1091-1094 (1994).
McClure et al., "The use of air-flow impedance to control fiber deposition patterns during electrospinning," Biomaterials 33: 771-779 (2012), doi: 10.1016/j.biomaterials.2011.10.011.
McMillan et al. "Small diameter porous poly (ε-caprolactone) films enhance adhesion and growth of human cultured epidermal keratinocyte and dermal fibroblast cells", Tissue Eng. Apr. 2007;13(4): pp. 789-798.
Mi et al. "Asymmetric chitosan membranes prepared by dry/west phase separation: a new type of wound dressing for controlled antibacterial release", Journal of Membrane Science, (vol. 212) pp. 237-254.
Murthy et al. "Biodegradation of Polymers" 2012, Polymer Science: A Comprehensive Reference, 9:547-560.
Norris et al. "Electrostatic fabrication of ultrafine conducting fibers: polyaniline/polyethylene oxide blends" Synthetic Metals 114 (2000) pp. 109-114.
Panseri et al., "Electrospun micro- and nanofiber tubes for functional nervous regeneration in sciatic nerve transections." BMC Biotechnol. Apr. 11, 2008;8:39.
Park, S. et al., Apparatus for Preparing Electrospun Nanofibers: Designing and Electrospinning process for Nanofiber Fabrication, Polymer International, 2007, pp. 1361-1366.
Pepper et al., "Factors Influencing Poor Outcomes in Synthetic Tissue-Engineered Tracheal Replacement" Otolaryngol Head Neck Surg. Sep. 2019; 161(3): 458-467.
Pham et al. "Electrospun poly (ε-caprolactone) microfiber and multilayer nanofiber/microfiber scaffold: characterization of scaffolds and measurement of cellular infiltration", Biomacromolecules 2006, pp. 7, 10, 2796-2805, Pub. Sep. 23, 2006.
Pham et al., "Electrospinning of Polymeric Nanofibers for Tissue Engineering Applications: A Review", Tissue Engineering, 12(5): 1197-1211 (2006).
Quan et al., "Aligned fibers enhance nerve guide conduits when bridging peripheral nerve defects focused on early repair stage." Neural Regeneration Research 14(5):p. 903-912, May 2019.
Ramakrishna et al., "Electrospun nanofibers: solving global issues," Materials Today 9: 40-50 (2006), doi: 10.1016/S1369-7021(06)71389-X.
Rieger et al. "Designing electrospun nanofiber mats to promote wound healing—a review," J. Mater. Chem. B, 2013, 1, 4531.
Schneider et al. "Influence of pH on Wound-healing: a New Perspective for Wound-therapy" 2007 Arch. Dermatol. Res. 298:413-420.
Shin, et al. "Experimental characterization of electrospinning: the electrically forced jet and instabilities" Polymer 42 (2001) 9955-9967.
Shin, Ho Joon, et al. "Electrospun PLGA nanofiber scaffolds for articular cartilage reconstruction: mechanical stability, degradation and cellular responses under mechanical simulation in vitro." Journal of Biomaterials Science, Polymer Edition 17.1-2 (2006) pp. 103-119.
Smith et al., "Suture-reinforced electrospun polydioxanone-elastin small-diameter tubes for use in vascular tissue engineering: a feasibility study," Acta Biomaterialia 4: 58-66 (2008), doi: 10.1016/j.actbio.2007.08.001.
Stitzel et al., "Arterial Smooth Muscle Cell Proliferation on a Novel Biomimicking, Biodegradeable Vascular Graft Scaffold," Journal of Biomaterials Applications 16: 22-33 (2001), doi: 10.1106/U2UU-M9QH-Y0BB-5GYL.
Subbiah et al. "Electrospinning of Nanofibers," J. of Applied Polymer Science, 96: 557-569 (2005).
Tan et al., "Tensile test of a single nanofiber using an atomic force microscope tip", Applied Physics Letters 86, 073115 (2005).
Teo W et al. "Electrospun scaffold tailored for tussie-specific extracellular matrix." Biotechnol J Healthc Nutr Technol. 2006;1(9):918-29.
Thomas et al. "Electrospun bioactive nanocomposite scaffolds of polycaprolactone and nanohydroxyapatite for bone tissue engineering", J Nanosci Nanotechnol. Feb. 2006;6(2):487-93. doi: 10.1166/jnn.2006.097.
Tormala, et al., "Ultra-High-Strength absorable self-reinforeced polyglycolide (SR-PGA) composite rods for internal fixation of bone fractures: In vitro and in vivo study" Journal of Biomedical Materials Research, Jan. 1991.
Valizadeh et al., "Electrospinning and electrospun nanofibres," IET Nanobiotechnol., 2014, vol. 8, Iss. 2, pp. 83-92.
Vaz et al. "Design of scaffold for blood vessel tissue engineering using a multiple-layering electrospinning technique" Acta Biomater/Sep. 2005;1(5):572-82. doi:10.1016/j.actbio.2005.06.006. Epub Jul. 26, 2005. https://pubmed.ncbi.nlm.nih.gov/16701837/.
WISE Histologic proof that acellular dermal matrices (ADM)-Enduragen DermaMalrix and DuraMatrix—are not repopulaled or nonviable and that AlloDerm may be repopulated but degraded synchronously. Aesthetic surgery Journal / the American Society for Aesthetic Plastic surgery 2012; vol. 32 pp. 355-358.
Wulkersdorfer, "Bimodal Porous Scaffolds by Sequential Electrospinning of Poly(glycolic acid) with Sucrose Particles," International Journal of Polymer Science 2010: 1-9 (2010), doi: 10.1155/2010/436178.
Xie et al., Putting electrospun nanofibers to work for biomedical research. Macromol Rapid Commun 2008; 29, 1775-1792.
Xie, et al., Conductive core-sheath nanofibers and their potential applications in neural tissue engineering. Adv Funct Mater 2009; 19, 2312-2318.
Xie, et al., Neurites outgrowth on nanofiber scaffolds with different orders, structures, and surface properties. ACS Nano 2009; 3, 1151-1159.
Xie, et al., Radially Aligned, Electrospun Nanofibers as Dural Substitutes for Wound Closure and Tissue Regeneration Applicalion, ACS Nano, 2010, vol. 4, No. 9, pp. 5027-5036.
Yarin, et al., "Taylor Cone and Jetting from Liquid Driplets in Electrospinning of Nanofibers," (2001). College of Polymer Science and Polymer Engineering. 85.
Yogeshwar et al., "Electrospinning of Type I Collagen and PCL Nanofibers Using Acetic Acid," Wiley Online Library, Feb. 1, 2012.
Zerris, et al., Repair of the dura mater with processed collagen devices. Journal of biomedical materials research Part B, Applied biomaterials 2007; vol. 83, pp. 580-588.
Zong, Xinhua, et al. "Structure and process relationship of electrospun bioabsorbable nanofiber membranes." Polymer 43.16 (2002) pp. 4403-4412.

(56) References Cited

OTHER PUBLICATIONS

Australian Examination Report issued for Application No. 2011268321, dated Apr. 17, 2015 (4 pages).
Australian Examination Report No. 1 issued for Application No. 2016406314 dated Oct. 29, 2020 (4 pages).
Australian Examination Report No. 1 issued for Application No. 2012390291 dated May 31, 2017 (4 pages).
Australian Examination Report No. 1 issued for Application No. 2017232208 dated Jan. 8, 2018 (4 pages).
Australian Examination Report No. 2 issued for Application No. 2016406314 dated 12, Mar. 2021.
Australian Examination Report No. 3 issued for Application No. 2016406314 dated Jul. 5, 2021.
Brazil Technical Report for related Application No. BR112012032169-2, dated Feb. 20, 2019, 4 pages.
Brazil Technical Report for related Application No. BR112015006301-2, dated Oct. 15, 2020, 5 pages.
Canadian Examiner's Report issued for Application No. 2,885,682, dated Jun. 4, 2018 (5 pages).
China Examiner's Report issued for Application No. 201680087078.9, dated Jan. 20, 2021 with translation in 28 pages.
China Second Office Action for Application No. 201680087078.9 dated Jul. 14, 2021 with translation in 28 pages.
European Examination Report issued for Application No. 12884789.4 dated Feb. 13, 2018 (5 pages).
European Extended Search Report in Application No. 16901840.5 dated Dec. 2, 2019 in 10 pages.
European Extended Search Report issued for Application No. 11796426.2, dated Mar. 27, 2014 (6 pages).
European Extended Search Report issued for U.S. Appl. No. 12/884,789, on Jun. 16, 2016 (12 pages).
European Office Action for application No. 16901840.5, dated Sep. 10, 2021.
European Search Report and Written Opinion for EP application No. 18164340, dated May 17, 2019, 5 pages.
European Search Report and Written Opinion for EP application No. 20175280.5, dated Sep. 11, 2020 in 8 pages.
European Supplementary Partial Search Report issued for U.S. Appl. No. 12/884,789, dated Feb. 29, 2016 (8 pages).
GCC Examination Report in Application No. GC 2017-33397 dated Apr. 15, 2019 in 4 pages.
Indian Examination Report issued for Application No. 11141/DELNP/2012, dated Jun. 21, 2018 (7 pages).
Indian First Examination Report for IN Application No. 2299/DELNP/2015, dated Oct. 24, 2019, 6 pages.
Indian Frist Examination Report for IN Application No. 201817046790, dated Sep. 29, 2021, 6 pages.
Japanese Office action issued for Application No. 2013-515511, dated Oct. 28, 2014.
Japanese Office Action Summary issued for Application No. 2015-533026, dated Oct. 18, 2016 (5 pages).
Japanese Office translation issued for Application No. 2015-533026, dated Jun. 27, 2017 (4 pages).
PCT International Preliminary Report on Patentability for PCT/US2011/040691, issued Dec. 19, 2012, 9 pages.
PCT International Search Report and Written Opinion issued for Application No. PCT/2011/040691, dated Feb. 24, 2012.
PCT International Search Report and Written Opinion of International Application No. PCT/US2012/056548 dated Apr. 26, 2013 in 14 pages.
PCT International Search Report in International Application No. PCT/US16/32001 dated Aug. 11, 2016 in 1 page.
Singapore Examination Report issued for Application No. 11201502207W, dated Jun. 13, 2017 (8 pages).
Singapore Search and Examination Report for SG 2012092888, issued May 15, 2014, 17 pgs.
Singapore Search and Examination Report for SG 2012092888, issued Jan. 30, 2015, 8 pgs.
International Search Report and Written Opinion in application No. PCT/IB2022/057029, mailed on Oct. 18, 2022, in 8 pages.
International Search Report and Written Opinion in application No. PCT/IB2022/057028, mailed on Jan. 6, 2023, in 9 pages.
International Search Report and Written Opinion in application No. PCT/US2022/75995, mailed on Feb. 3, 2023, in 18 pages.
Declaration of Gary E. Wnek, PH.D. in support of Petition for Inter Partes Review of U.S. Pat. No. 10,632,228.
Defendants' Initial Invalidity Contentions in Civil Action No. 20-980-CFC-JLH dated Nov. 4, 2021 in 618 pages.
Petition for Inter Partes Review of U.S. Pat. No. 10,632,228 dated May 28, 2021 in 91 pages.
Report and Recommendation filed May 25, 2023, in Case No. 1:20-cv-00980-CFC-JLH, Document 201, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and *Nanofiber Solutions, LLC, and The Research Foundation for the State University of New York*, Counterclaim Plaintiffs, v. *Acera Surgical, Inc.*, Counterclaim Defendant, in 11 pages.
Joint Appendix to Claim Construction Brief filed Mar. 31, 2023, in Case No. 1:20-cv-00980-CFC-JLH, Document 192, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and Related Counterclaims, in 898 pages.
Joint Claim Construction Brief Regarding U.S. Pat. No. 11,224,677, filed Mar. 31, 2023, in Case No. 1:20-cv-00980-FCF-JLH, Document 191, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and Related Counterclaims, in 86 pages.
Joint Claim Construction Chart, filed Mar. 30, 2023, in Case No. 1:20-cv-00980-CFC-JLH, Document 188, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and Related Counterclaims, in 39 pages.
Report and Recommendation filed Oct. 12, 2022, in Case No. 1:20-cv-00980-CFC-JLH, Document 147, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and *Nanofiber Solutions, LLC, and The Research Foundation for the State University of New York*, Counterclaim Plaintiffs, v. *Acera Surgical, Inc.*, Counterclaim Defendant, in 24 pages.
Joint Claim Construction Brief, filed Jul. 29, 2022, in Case No. 1:20-cv-00980-CFC-JLH, Document 120, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and Related Counterclaims, in 79 pages.
Joint Appendix to Claim Construction Brief filed Jul. 29, 2022, Document 121, in Case No. 1:20-CV-00980-CFC-JLH, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and Related Counterclaims, in 731 pages.
Joint Claim Construction Chart, filed May 10, 2022, Document 99, in Case No. 1:20-CV-00980-CFC-JLH, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and Related Counterclaims, in 273 pages.
Joint Claim Construction Chart filed Feb. 7, 2023, Document 172, in Case No. 1:20-CV-00980-CFC-JLH, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and Related Counterclaims, in 57 pages.
Plaintiffs Acera Surgical, Inc., Retectix, LLC and Washington University's Objections to the Report and Recommendation [D.I 147} filed Oct. 26, 2022, in Case No. 1:20-CV-00980-CFC-JLH, *Acera Surgical, Inc., Retectix, LLC, and Washington University*, Plaintiffs, v. *Nanofiber Solutions, LLC, Paragen Technologies LLC,*

(56) References Cited

OTHER PUBLICATIONS

*Atreon Orthopedics LLC, and Renovoderm LLC*, Defendants, and Related Counterclaims, in 18 pages.

\* cited by examiner

1mm

100 μm

20 μm

20 μm

1mm scale bar for 5A-5D

20 µm     10 µm

PARTICLE-FORM HYBRID-SCALE FIBER MATRIX

BACKGROUND

Field

Embodiments of the disclosure generally related to particle forms of a nanofiber and/or hybrid-scale fiber matrix having the architecture of said matrix.

Description

Numerous pathological conditions and surgical procedures result in substantial defects in a variety of organs, tissues, and anatomical structures. In the majority of such cases, surgeons and physicians are required to repair such defects utilizing specialized types of surgical meshes, materials, and/or scaffolds. Unfortunately, the in vivo performance of known surgical materials is negatively impacted by a number of limiting factors. For instance, existing synthetic surgical meshes typically result in excessive fibrosis or scarification leading to poor tissue integration and increased risk of post-operative pain. Simultaneously, known biologic materials may induce strong immune reactions and aberrant tissue ingrowth which negatively impact patient outcomes. Additionally, existing synthetic surgical meshes can create scarification, post-operative pain, limited mobility, limited range of motion, adhesions, infections, erosion, poor biomechanical properties, and/or poor intraoperative handling.

Nanofabricated, nanofiber, or hybrid-scale fiber matrices are meshes or materials composed of reabsorbable polymer fibers tens to thousands of times smaller than individual human cells, which have recently been proposed as a unique substrate for implantable surgical meshes and materials. Generally, existing nanofiber materials tend to possess suboptimal mechanical performance compared to known surgical meshes. Existing nanofiber materials do not possess the tensile strength, tear resistance, and burst strength needed for numerous surgical applications or for basic intraoperative handling prior to in vivo placement. To combat this deficiency, known meshes are formed using higher fiber densities as a means of improving mechanical strength. Yet, utilization of such high-density meshes can decrease effective cellular ingrowth into the mesh, decrease mesh integration with native tissue, and reduce the biocompatibility of the polymeric implant. As a result, nanofiber or hybrid-scale fiber matrix materials with increased thickness and/or strength and favorable cellular and/or tissue integration and biocompatibility are needed as well as a method for producing nanofiber or hybrid-scale fiber matrix materials.

Repairs to tissues may be facilitated by one or more materials as described herein, including polymeric materials or processed tissue that acts like the native tissue in question. For example, skin wounds, including those caused by trauma or deliberately during a medical procedure, may be repaired by application of materials with favorable cellular and tissue integration. To facilitate repair of skin wounds, dressings and other coverings may be applied in both clinical and surgical settings, to promote healing and protect the wound from further harm. Typical wound dressings have a variety of purposes, including absorption of exudate, debriding of foreign material and dead cellular matter, stemming bleeding, protecting from infection, and the easing of pain, as well as generally promoting the healing process. As another example, neurosurgical repairs may be effected using one or more materials described herein.

Wounds, including but not limited to abrasions, lacerations, punctures, ruptures, and penetrating wounds may result in regular or irregularly shaped damage to the skin and underlying tissues. Depending on the shape, location, and underlying tissues of the wound, various methods to facilitate repair and manage possible concomitant complications are available in a clinical or surgical setting. To facilitate repair of wounds, healthcare providers may utilize coverings and other barriers to occlude and prevent entry of foreign material to the wound site, or otherwise may be left exposed without coverings under medical supervision.

In addition while cell microarrays may be useful in biomedical research and tissue engineering, at least some known techniques for producing such cell microarrays may be costly and time consuming, and may require the use of specialized, sophisticated instrumentation.

SUMMARY

Various embodiments described herein relate to a plurality of particles, including particulates, powder, milled material, granules, motes, among others and methods for forming said plurality of particles. In particular, in some embodiments, described herein are a plurality of particles configured to improve wound healing, the plurality of particles comprises: a D50 of between 1 μm and 5000 μm; wherein the plurality of particles are formed by breaking down a sheet of electrospun graft material, wherein the electrospun graft material possesses a hybrid-scale fiber matrix; and wherein the plurality of particles include the hybrid-scale fiber matrix of the electrospun graft material. In some embodiments of the plurality of particles, the plurality of particles are mixed with other fibers or nonfibrous structures. In some embodiments of the plurality of particles, the sheet of electrospun graft material comprises a plurality of electrospun fibers, the plurality of electrospun fibers formed by electrospinning a first fiber composition and a second fiber composition, the first fiber composition comprising poly(lactic-co-glycolic acid), and the second fiber composition comprising polydioxanone. In some embodiments of the plurality of particles, wherein the sheet of electrospun graft material comprises a plurality of electrospun fibers, the plurality of electrospun fibers formed by electrospinning a first fiber composition and a second fiber composition, the first fiber composition different from the second fiber composition.

In some embodiments, the plurality of particles are described wherein the first fiber composition comprises a polymer selected from one or more of: polycaprolactone (poly(ε-caprolactone), PCL), polydioxanone (PDO), poly(glycolic acid) (PGA), poly(L-lactic acid) (PLA), poly(lactide-co-glycolide) (PLGA), poly(L-lactide) (PLLA), poly(D,L-lactide) (P(DLLA)), poly(ethylene glycol) (PEG), montmorillonite (MMT), poly(L-lactide-co-ε-caprolactone) (P(LLA-CL)), poly(ε-caprolactone-co-ethyl ethylene phosphate) (P(CL-EEP)), poly[bis(p-methylphenoxy)phosphazene] (PNmPh), poly(3-hydroxybutyrate-co-3-hydroxyvalerate) (PHBV), poly(ester urethane) urea (PEUU), poly (p-dioxanone) (PPDO), polyurethane (PU), polyethylene terephthalate (PET), poly(ethylene-co-vinylacetate) (PEVA), poly(ethylene oxide) (PEO), poly(phosphazene), poly(ethylene-co-vinyl alcohol), polymer nanoclay nanocomposites, poly(ethylenimine), poly(ethyleneoxide), poly vinylpyrrolidone; polystyrene (PS), biologically derived and natural materials including collagen, elastin, laminin, fibrin, among others, and combinations thereof. Particularly suitable polymers include poly(lactic-co-glycolic acid), polydioxanone, polycaprolactone, or combinations thereof, and; wherein the second fiber composition comprises a polymer selected from one or more of: polycaprolactone (poly(ε-caprolactone), PCL), polydioxanone (PDO), poly(glycolic acid) (PGA), poly(L-lactic acid) (PLA), poly(lactide-co-glycolide) (PLGA), poly(L-lactide) (PLLA), poly(D,L-lactide) (P(DLLA)), poly(ethylene glycol) (PEG), montmorillonite (MMT), poly(L-lactide-co-ε-caprolactone) (P(LLA-CL)), poly(ε-caprolactone-co-ethyl ethylene phosphate) (P(CL-EEP)), poly[bis(p-methylphenoxy)phosphazene] (PNmPh), poly(3-hydroxybutyrate-co-3-hydroxyvalerate) (PHBV), poly(ester urethane) urea (PEUU), poly(p-dioxanone) (PPDO), polyurethane (PU), polyethylene terephthalate (PET), poly(ethylene-co-vinylacetate) (PEVA), poly (ethylene oxide) (PEO), poly(phosphazene), poly(ethylene-co-vinyl alcohol), polymer nanoclay nanocomposites, poly (ethylenimine), poly(ethyleneoxide), poly vinylpyrrolidone; polystyrene (PS), biologically derived and natural materials including collagen, elastin, laminin, fibrin, among others, and combinations thereof. Particularly suitable polymers include poly(lactic-co-glycolic acid), polydioxanone, polycaprolactone, or combinations thereof. In some embodiments of the plurality of particles, the plurality of particles are configured to be mixed with fluid to create an injectable solution. In some embodiments, the plurality of particles are sorted based on physical or mechanical properties. In some embodiments the plurality of particles are sorted based on one or more of: surface area, mass, size, shape, density, pourability, deployability, flowability, charge, viscosity, color, or reflectivity. In some embodiments, the particles are configured to be placed directly onto a wound site. In some embodiments, the plurality of particles are incorporated into a hydrogel. In some embodiments, the plurality of particles having a first and second fiber composition are configured so that the ratio of the first fiber composition to the second fiber composition can range from about 1:10 to about 10:1. In some embodiments, the plurality of particles are further combined with one or more of: bone marrow aspirate, platelet rich plasma, other powders, other polymers including electrospun sheets, drugs, cells, growth factors, radioactive agents, chemical agents, or bioactive agents. In some embodiments, the plurality of particles are configured to be applied to a suture line.

Also described is a method of forming a plurality of particles configured to improve wound healing, the method comprises: electrospinning a non-woven sheet of a hybrid-scale fiber matrix; breaking down the hybrid-scale fiber matrix into a plurality of particles; and collecting the plurality of particles; wherein the plurality of particles include the structure or nanostructure of the hybrid-scale fiber matrix. In some embodiments, the plurality of particles have a D50 of between 1 µm and 5000 µm. In some embodiments, the method further comprises freezing the hybrid-scale fiber matrix prior to milling, breaking, cutting, and/or general processing of the polymer into a desired form. In some embodiments, the method further comprises post processing of the plurality of particles. In some embodiments, the post processing comprises one or more of: nitrogen backfilling, antistatic treatment, or size separation. In some embodiments, the post processing comprises separation of the plurality of particles based on physical or mechanical characteristics. In some embodiments, the physical or mechanical characteristics include: surface area, mass, size, shape, density, pourability, deployability, flowability, charge, viscosity, color, or reflectivity. In some embodiments, the breaking down comprises ultrasonification. In some embodiments, the breaking down comprises cutting the non-woven sheet. In some embodiments, the cutting of the non-woven sheet comprises cryo-cutting or cryo-milling, or other cutting techniques.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

DETAILED DESCRIPTION

Figure 1:
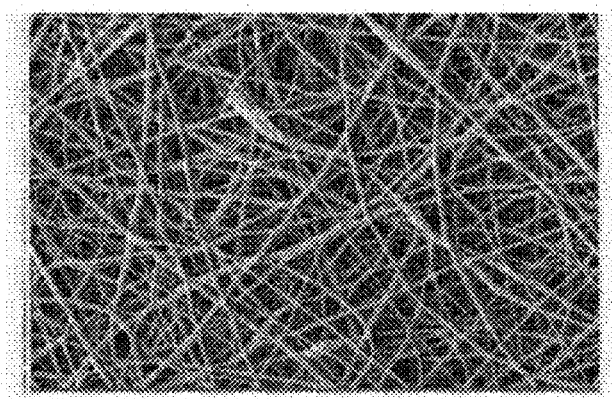
FIG. 1 illustrates a scanning electron micrograph of an embodiment of a non-woven fiber composition of the disclosure.

Embodiments provided herein facilitate repairing biological tissue or reinforcing biomedical material based on a biomedical patch (e.g., graft, hybrid-scale fiber matrix or matrices, sheet) including a plurality of fibers, such as shown in FIG. 1. Such fibers may have a very small cross-sectional diameter (e.g., from 1-3000 nanometers, from 1-1000 nanometers, from 1 nanometer-10 millimeters) and, accordingly, may be referred to as hybrid-scale fiber matrices and/or microfibers. While biomedical patches are described herein with reference to dura mater and use as a surgical mesh, embodiments described may be applied to any biological tissue. Moreover, although described as biomedical patches, structures with aligned fibers may be used for other purposes. Accordingly, embodiments described are not limited to biomedical patches.

Patches may be described in further detail in U.S. Pat. Pub. Nos. 2017/0326270 and 2017/0319323, as well as U.S. Pat. No. 10,124,089, the entirety of each of which is hereby incorporated by reference in their entirety.

Generally, the present disclosure is directed to particles formed from non-woven graft materials including two or more distinct types of fiber compositions, each of which possesses independent mechanical, chemical and/or biological properties. For example, in one embodiment, inclusion of one fiber composition can stabilize the resulting non-woven graft material, while the other fiber composition can improve stability, free-shrinkage properties, mechanical properties, and resorption rate of the non-woven graft material.

As used interchangeably herein, "non-woven graft material" and "non-woven graft fabric" refer to a material having a structure of individual fibers or threads which are interlaid, but not in an identifiable manner as in a knitted fabric or a woven fabric. Non-woven graft materials and non-woven graft fabrics can be formed from many processes such as for example, electrospinning processes, meltblowing processes, spunbonding processes, melt-spraying and bonded carded web processes. The basis weight of non-woven graft materials is usually expressed in ounces of material per square yard (osy) or grams per square meter (gsm) and the fiber diameters are usually expressed in nanometers and micrometers (microns). Suitable basis weight of non-woven graft materials of the present disclosure can range from about 50 gsm to about 300 gsm. More suitably, basis weight of non-woven graft materials of the present disclosure can range from about 70 gsm to about 140 gsm. The tensile strength of the non-woven graft material of the present disclosure can range from about 5 Newtons (N) to about 50 Newtons (N), including from about 1 N to about 10 N to about 15 N. The strength of the non-woven graft material of the present disclosure can also be described in terms of suture pull-out strength, which refers to the force at which a suture can be torn from the non-woven graft material. Suitable suture pull-out strength can range from about 1 N to about 5 N.

As used herein the term "microfibers" refers to small diameter fibers having an average diameter not greater than 75 microns, for example, having an average diameter of from about 0.5 microns to about 50 microns, or more particularly, microfibers having an average diameter of from about 2 microns to about 40 microns. Another frequently used expression of fiber diameter is denier. The diameter of a polypropylene fiber given in microns, for example, may be converted to denier by squaring, and multiplying the result by 0.00629, thus, a 15 micron polypropylene fiber has a denier of about 1.42 (152×0.00629=1.415).

As used herein, the terms "nano-sized fibers" or "nanofibers" refer to very small diameter fibers having an average diameter not greater than 2000 nanometers, than 1000 nanometers, and suitably, not greater than 1500 nanometers (nm). Nanofibers are generally understood to have a fiber diameter range of about 10 to about 1500 nm, more specifically from about 10 to about 1000 nm, more specifically still from about 20 to about 500 nm, and most specifically from about 20 to about 400 nm. Other exemplary ranges include from about 50 to about 500 nm, from about 100 to 500 nm, or about 40 to about 200 nm.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. Nos. 3,502,763 and 3,909,009 to Levy, and U.S. Pat. No. 3,542,615 to Dobo et al., the entirety of each of which is hereby incorporated by reference in their entirety.

As used herein the term "meltblown fibers" refers to fibers formed by extruding a molten thermoplastic material through a plurality of fine, usually circular, die capillaries as molten threads or filaments into converging high velocity gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form randomly disbursed meltblown fibers. Such a process is disclosed, for example, in U.S. Pat. No. 3,849,241, which is hereby incorporated by reference in its entirety. Meltblown fibers are microfibers which may be continuous or discontinuous and are generally smaller than 10 microns in diameter.

As used herein, the term "electrospinning" refers to a technology which produces nano-sized fibers referred to as electrospun fibers from a solution using interactions between fluid dynamics and charged surfaces. In general, formation of the electrospun fiber involves providing a solution to an orifice in a body in electric communication with a voltage source, wherein electric forces assist in forming fine fibers that are deposited on a surface that may be grounded or otherwise at a lower voltage than the body. In electrospinning, a polymer solution or melt provided from one or more needles, slots or other orifices is charged to a high voltage relative to a collection grid. Electrical forces overcome surface tension and cause a fine jet of the polymer solution or melt to move towards the grounded or oppositely charged collection grid. The jet can splay into even finer fiber streams before reaching the target and is collected as interconnected small fibers. Specifically, as the solvent is evaporating (in processes using a solvent), this liquid jet is stretched to many times it original length to produce continuous, ultrathin fibers of the polymer. The dried or solidified fibers can have diameters of about 40 nm, or from about 10 to about 100 nm, although 100 to 500 nm fibers are commonly observed. Various forms of electrospun nanofiber or hybrid-scale fiber matrices include branched nanofiber or hybrid-scale fiber matrices, tubes, ribbons and split nanofiber or hybrid-scale fiber matrices, nanofiber or hybrid-scale fiber matrix yarns, surface-coated nanofiber or hybrid-scale fiber matrices (e.g., with carbon, metals, etc.), nanofiber or hybrid-scale fiber matrices produced in a vacuum, and so forth. The production of electrospun fibers is illustrated in many publication and patents, including, for example, P. W. Gibson et al., "Electrospun Fiber Mats: Transport Properties," AIChE Journal, 45(1): 190-195 (January 1999), which is hereby incorporated herein by reference in its entirety.

As used herein, the term "type" such as when referring to "different types of fibers" or "distinct types of fibers" refers to fibers having "a substantially different overall material composition" with measurably different properties, outside of "average diameter" or other "size" differences. That is, two fibers can be of the same "type" as defined herein, yet have different "average diameters" or "average diameter ranges." Although fibers are of different "types" when they have a substantially different overall material composition, they can still have one or more components in common. For example, electrospun fibers made from a polymer blend with a first polymeric component present at a level of at least 10 wt % would be considered a different fiber type relative to electrospun fibers made from a polymer blend that was substantially free of the first polymeric component. Fibers of different "types" can also have a completely different content, each made of a different polymer for example, or one made from a polymer fiber and the other from a titania fiber, or a ceramic fiber and a titania fiber, and so on.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configuration of the material. These configurations include, but are not limited to isotactic and atactic symmetries.

Hybrid-Scale Fiber Matrix Graft Material

The non-woven graft materials of the present disclosure typically include at least two distinct types of fiber compositions, each of which possesses independent mechanical, chemical and/or biological properties. However, in some embodiments the fibers can be the same. The fiber compositions are suitably made of synthetic resorbable polymeric materials. As used herein, the term "resorbable polymeric material" refers to material formed from resorbable (also referred to as "bioabsorbable") polymers; that is the polymers possess the property to break down when the material is exposed to conditions that are typical of those present in a post-surgical site into degradation products that can be removed from the site within a period that roughly coincides with the period of post-surgical healing. Such degradation products can be absorbed into the body of the patient. The period of post-surgical healing is to be understood to be the period of time measured from the application of the non-woven graft material of the present disclosure to the time that the post-surgical site is substantially healed. This period can range from a period of several days to several months depending on the invasiveness of the surgical and the speed of healing of the particular individual. It is intended that the subject non-woven graft material can be prepared so that the time required for resorption of the non-woven graft material can be controlled to match the time necessary for healing or tissue reformation and regeneration. For example, in some non-woven graft materials of the present disclosure, the fiber compositions are selected to degrade within a period of about one week, while in other non-woven graft materials, the compositions are selected to degrade within a period of three years, or even longer if desired.

The fiber compositions used in the present disclosure can be produced from any resorbable material that meets the criteria of that material as those criteria are described above. The fiber compositions can be formed from resorbable polymers such as (but not limited to) polymers of lactic and glycolic acids, copolymers of lactic and glycolic acids, poly(ether-co-esters), poly(hydroxybutyrate), polycaprolactone, copolymers of lactic acid and ε-aminocapronic acid, lactide polymers, copolymers of poly(hydroxybutyrate) and 3-hydroxyvalerate, polyesters of succinic acid, poly(N-acetyl-D-glucosamine), polydioxanone, cross-linked hyaluronic acid, cross-linked collagen, and the like, and combinations thereof. Suitable synthetic polymers can be, for example, polycaprolactone (poly(ε-caprolactone), PCL), polydioxanone (PDO), poly(glycolic acid) (PGA), poly(L-lactic acid) (PLA), poly(lactide-co-glycolide) (PLGA), poly (L-lactide) (PLLA), poly(D,L-lactide) (P(DLLA)), poly(ethylene glycol) (PEG), montmorillonite (MMT), poly(L-lactide-co-ε-caprolactone) (P(LLA-CL)), poly(ε-caprolactone-co-ethyl ethylene phosphate) (P(CL-EEP)), poly[bis(p-methylphenoxy)phosphazene] (PNmPh), poly(3-hydroxybutyrate-co-3-hydroxyvalerate) (PHBV), poly(ester urethane) urea (PEUU), poly(p-dioxanone) (PPDO), polyurethane (PU), polyethylene terephthalate (PET), poly(ethylene-co-vinylacetate) (PEVA), poly(ethylene oxide) (PEO), poly(phosphazene), poly(ethylene-co-vinyl alcohol), polymer nanoclay nanocomposites, poly(ethylenimine), poly (ethyleneoxide), poly vinylpyrrolidone; polystyrene (PS) and combinations thereof. Particularly suitable polymers include poly(lactic-co-glycolic acid), polydioxanone, polycaprolactone, and combinations thereof.

The fibers for the fiber compositions, including hybrid-scale fiber matrix fibers, may be of a variety of sizes as deemed suitable by one skilled in the art for the end purpose of the non-woven graft material. Typically, the fibers have a mean fiber diameter of less than 5 μm, including less than 2 μm, including less than 1.5 μm, and including less than 1.0 μm. For example, in some embodiments, the fibers can have a mean fiber diameter ranging from about 10 nm to about 5 μm, more specifically from about 10 nm to about 1.0 μm, more specifically still from about 20 nm to about 500 nm, and most specifically from about 20 nm to about 400 nm. Other exemplary ranges include from about 50 nm to about 500 nm, from about 100 nm to about 500 nm, and about 40 nm to about 200 nm.

Suitable ratios of the first fiber composition to the second fiber composition resulting in the non-woven graft material can range from about 10 to 1 to about 1 to 10.

In some embodiments, the non-woven graft material is made from a first non-woven fiber composition prepared from poly(lactic-co-glycolic acid) and a second non-woven fiber composition prepared from polydioxanone. The resultant non-woven graft material is a non-biologic tissue substitute designed to provide optimal strength, handling, and suturability, while reducing local inflammation to provide improved wound healing and tissue regeneration. In an exemplary embodiment the non-woven graft material can be synthesized by electrospinning a first fiber composition including a copolymer of glycolide and L-lactide and a second fiber composition including polydioxanone (100 mol %) to create an architecture that is reminiscent of native extracellular matrix. The glycolide mol % to L-lactide mol % can range from about 100 mol % glycolide to 0 mol % L-lactide to 0 mol % glycolide to about 100 mol % L-lactide. A particularly suitable non-woven graft material includes a first fiber composition including a copolymer of glycolide and L-lactide having a glycolide mol % to L-lactide mol % ratio of 90 mol % glycolide and 10 mol % L-lactide. This method of synthesis creates a material that is mechanically strong, while providing the look and feel of native tissue. The architecture of this non-biologic graft material furthermore supports tissue ingrowth and neoduralization with minimal inflammation.

The non-woven graft material typically can be prepared to be any of a variety of sizes, shapes and thicknesses. Wet and dry non-woven graft material can suitably be cut and trimmed to any desired size and shape. In particularly suitable embodiments, the non-woven graft material has a size ranging from about 0.55 in diameter disc, 0.5 in×1 in, 2.5 cm×2.5 cm (1 in×1 in) to about 25.5 cm×50 cm (10 in×20 in), including for example, from about 2.5 cm×2.5 cm (1 in×1 in), from about 5.0 cm×5.0 cm (2 in×2 in), from about 7.5 cm×7.5 cm (3 in×3 in), from about 12.5 cm×17.5 cm (5 in×7 in), and including about 10 cm×12.5 (4 in×5 in).

The non-woven graft materials typically have a thickness ranging from about 0.1 mm to about 5 mm, including from about 0.3 mm to about 0.8 mm, about 0.3 mm to about 0.7 mm, and about 0.3 mm to about 0.5 mm The non-woven graft material is typically porous, and has interconnecting pores having a pore size in the range of from about 10 μm2 to about 10,000 μm2. Particularly suitable embodiments have a pore size of less than 300 µm2. It is believed that pores of this size range can accommodate penetration by cells and can support the growth and proliferation of cells, followed by vascularization and tissue development.

In some aspects, the non-woven graft materials can be surface-modified with biomolecules such as (but not limited to) hyaluronans, collagen, laminin, fibronectin, growth factors, integrin peptides (Arg-Gly-Asp; i.e., RGD peptides), and the like, or by sodium hyaluronate and/or chitosan niacinamide ascorbate, which are believed to enhance cell migration and proliferation, or any combination thereof. The material can also be impregnated with these and other bioactive agents such as drugs, vitamins, growth factors, therapeutic peptides, and the like. In addition, drugs that would alleviate pain may also be incorporated into the material.

In another aspect, the present disclosure is directed to a laminate comprising a non-woven graft material, wherein the non-woven graft material includes a first non-woven fiber composition and a second non-woven fiber composition.

In some embodiments, the non-woven graft material of the laminate includes a first non-woven fiber composition including poly(lactic-co-glycolic acid) and a second non-woven fiber composition including polydioxanone, as described herein.

In some embodiments, the non-woven graft material can include at least one projection arising from a surface of the non-woven graft material. The projection is a protrusion or bulge arising from a surface of the non-woven graft material. The projection can arise from a top surface of the non-woven graft material, a bottom surface of the non-woven graft material, and a top surface and a bottom surface of the non-woven graft material. The projection can be any desired shape such as, for example, circular, spherical, square, rectangular, diamond, star, irregular, and combinations thereof. The projection can be any desired height as measured from the surface of the material to the top of the projection. In one embodiment, the projection can have a substantially uniform height from the surface of the material. In another embodiment, the projection can further form gradually from the surface of the material to the highest measurable surface of the projection. In some embodiments, a surface of the non-woven graft material includes a plurality of protrusions. The plurality of protrusions can be patterned or randomly distributed on a surface of the non-woven graft material. In another embodiment, the method includes forming at least one indentation in a surface of the non-woven graft material. The indentation is a recess or depression in a surface of the non-woven graft material. The indentation can in a top surface of the non-woven graft material, a bottom surface of the non-woven graft material, and a top surface and a bottom surface of the non-woven graft material. The indentation can be any desired shape such as, for example, circular, spherical, square, rectangular, diamond, star, irregular, and combinations thereof. The indentation can be any desired depth as measured from the surface of the material to the bottom of the indentation. In one embodiment, the indentation can have a substantially uniform depth from the surface of the material to the deepest depth of the indentation. In another embodiment, the indentation can further form gradually from the surface of the material to the deepest depth of the indentation. In some embodiments, a surface of the non-woven graft material includes a plurality of indentations. The plurality of indentations can be patterned or randomly distributed on a surface of the non-woven graft material. In another embodiment, the non-woven graft material can include at least one projection arising from a surface of the non-woven graft material and at least one indentation in the surface of the non-woven graft material. In another embodiment, the non-woven graft material can include at least one projection arising from a top surface of the non-woven graft material and at least one indentation in the top surface of the non-woven graft material. In another embodiment, the non-woven graft material can include at least one projection arising from a bottom surface of the non-woven graft material and at least one indentation in the bottom surface of the non-woven graft material. In another embodiment, the non-woven graft material can include at least one projection arising from a top surface of the non-woven graft material, at least one projection arising from a bottom surface of the non-woven graft material, at least one indentation in the top surface of the non-woven graft material, and at least one indentation in the bottom surface of the non-woven graft material. The plurality of indentations can be patterned or randomly distributed on a surface of the non-woven graft material. Suitable methods for forming projections and indentations include pressing, stamping, and other methods known to those skilled in the art.

Electrospinning

In some embodiments, the present disclosure is directed to methods of preparing the non-woven graft materials. The methods generally include preparing aqueous solutions of the polymers described above. Particularly, fibers resulting from separate polymer solutions can be contacted together using one or more processes such as electrospinning, electrospraying, melt-blowing, spunbonding, to form the non-woven graft material; and drying the non-woven graft material.

The non-woven graft material is dried to remove solvents used to prepare the aqueous polymer solutions. Drying can be done using methods generally known in the art, including, without limitation, Yankee dryers, vacuum ovens, vacuum chambers, and through-air dryers. Preferably, a non-compressive drying method that tends to preserve the bulk or thickness of the non-woven graft material is employed. Suitable through-drying apparatus and through-drying fabrics are conventional and well-known. One skilled in the art can readily determine the optimum drying gas temperature and residence time for a particular through-drying operation.

In some embodiments, a first fiber composition resulting from a first aqueous polymer solution and a second fiber composition resulting from a second aqueous polymer solution are blended to form a non-woven graft material using the electrospinning process as described above. The electrospinning process generally involves applying a high voltage (e.g., about 1 kV to about 100 kV, including about 3 kV to about 80 kV, depending on the configuration of the electrospinning apparatus) to a polymer fiber solution to produce a polymer jet. As the jet travels in air, the jet is elongated under repulsive electrostatic force to produce nanofibers or hybrid-scale fiber matrix fibers from the polymer fiber solution. The high voltage is applied between the grounded surface (or oppositely charged surface) and a conducting capillary into which a polymer fiber solution is injected. The high voltage can also be applied to the solution or melt through a wire if the capillary is a nonconductor such as a glass pipette. Initially the solution at the open tip of the capillary is pulled into a conical shape (the so-called "Taylor cone") through the interplay of electrical force and surface tension. At a certain voltage range, a fine jet of polymer fiber solution forms at the tip of the Taylor cone and shoots toward the target. Forces from the electric field accelerate and stretch the jet. This stretching, together with evaporation of solvent molecules, causes the jet diameter to become smaller. As the jet diameter decreases, the charge density increases until electrostatic forces within the polymer overcome the cohesive forces holding the jet together (e.g., surface tension), causing the jet to split or "splay" into a multifilament of polymer nanofibers or hybrid-scale fiber matrix fibers. The fibers continue to splay until they reach the collector, where they are collected as nonwoven nanofibers or hybrid-scale fiber matrix fibers, and are optionally dried.

Suitable solvents for preparing aqueous polymer solutions include, for example, hexafluoroisopropanol (HFIP), dichloromethane (DCM), dimethylformamide (DMF), acetone, and ethanol.

In some embodiments, the method can further include forming at least one projection arising from a surface of the non-woven graft material, forming at least one indentation in a surface of the non-woven graft material, and combinations thereof. The projection is a protrusion or bulge arising from a surface of the non-woven graft material. The projection can arise from a top surface of the non-woven graft material, a bottom surface of the non-woven graft material, and a top surface and a bottom surface of the non-woven graft material. The projection can be any desired shape such as, for example, circular, spherical, square, rectangular, diamond, star, irregular, and combinations thereof. The projection can be any desired height as measured from the surface of the material to the top of the projection. In one embodiment, the projection can have a substantially uniform height from the surface of the material. In another embodiment, the projection can further form gradually from the surface of the material to the highest measurable surface of the projection. In some embodiments, a surface of the non-woven graft material includes a plurality of protrusions. The plurality of protrusions can be patterned or randomly distributed on a surface of the non-woven graft material. In another embodiment, the method includes forming at least one indentation in a surface of the non-woven graft material. The indentation is a recess or depression in a surface of the non-woven graft material. The indentation can in a top surface of the non-woven graft material, a bottom surface of the non-woven graft material, and a top surface and a bottom surface of the non-woven graft material. The indentation can be any desired shape such as, for example, circular, spherical, square, rectangular, diamond, star, irregular, and combinations thereof. The indentation can be any desired depth as measured from the surface of the material to the bottom of the indentation. In one embodiment, the indentation can have a substantially uniform depth from the surface of the material to the deepest depth of the indentation. In another embodiment, the indentation can further form gradually from the surface of the material to the deepest depth of the indentation. In some embodiments, a surface of the non-woven graft material includes a plurality of indentations. The plurality of indentations can be patterned or randomly distributed on a surface of the non-woven graft material. In another embodiment, the non-woven graft material can include at least one projection arising from a surface of the non-woven graft material and at least one indentation in the surface of the non-woven graft material. In another embodiment, the non-woven graft material can include at least one projection arising from a top surface of the non-woven graft material and at least one indentation in the top surface of the non-woven graft material. In another embodiment, the non-woven graft material can include at least one projection arising from a bottom surface of the non-woven graft material and at least one indentation in the bottom surface of the non-woven graft material. In another embodiment, the non-woven graft material can include at least one projection arising from a top surface of the non-woven graft material, at least one projection arising from a bottom surface of the non-woven graft material, at least one indentation in the top surface of the non-woven graft material, and at least one indentation in the bottom surface of the non-woven graft material. The plurality of indentations and the plurality of indentations can be patterned or randomly distributed on a surface of the non-woven graft material. Suitable methods for forming projections and indentations include pressing, stamping, and other methods known to those skilled in the art.

Particles

Figure 2:
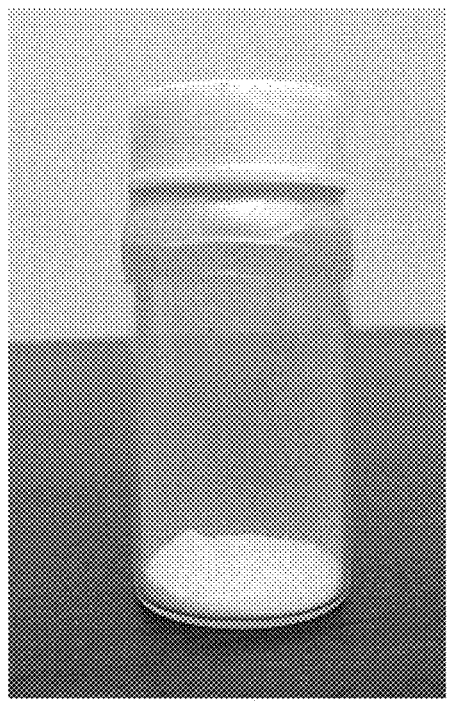
FIG. 2 illustrates a photographic image of particles of embodiments of graft materials.
Figure 3:
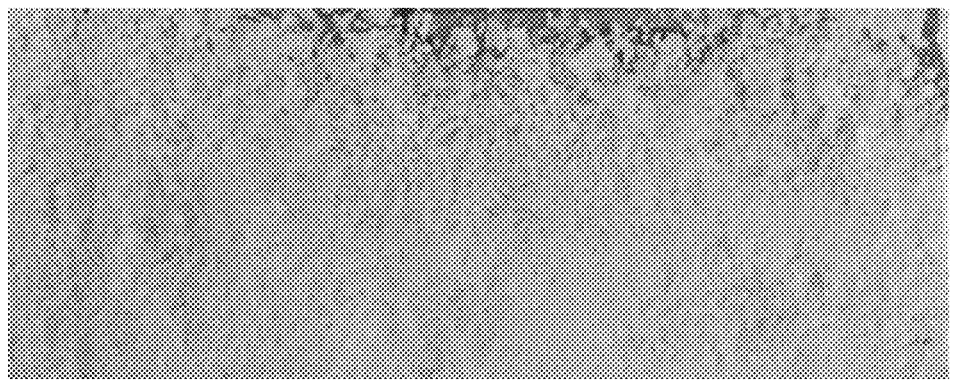
FIG. 3 illustrates a photographic image of particles of embodiments of graft materials.
Figure 4A:
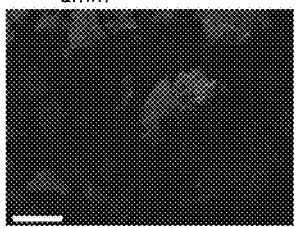
FIGS. 4A-4E illustrates a series of scanning electron micrographs of an embodiment of a non-woven fiber composition of the disclosure, illustrating fiber morphology at different magnifications.
Figure 4B:
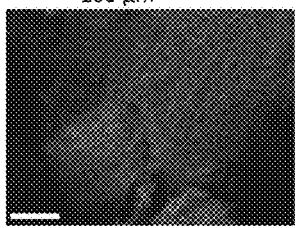
Figure 4C:
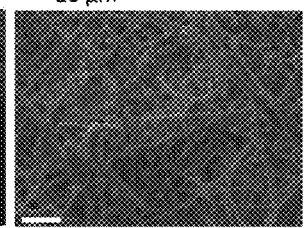
Figure 4D:
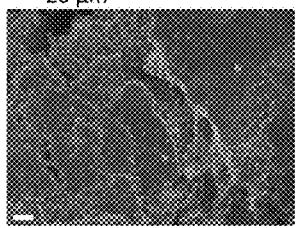
Figure 4E:
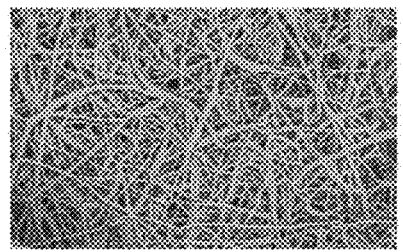

Once the graft material (e.g., electrospun sheet) is formed with the nanostructure or hybrid-scale fiber matrix discussed herein, the graft material can be broken down into small, such as micro- or nano-scale, components (e.g., particles, powder, balls comprising a hybrid-scale fiber matrix) such as shown in FIG. 2 and FIG. 3. Advantageously, the small nanofibers or hybrid-scale fiber matrix components can maintain the overall fiber hybrid-scale fiber structure of the original graft material, wherein particles retain parent fiber morphology, and which can be evidenced by imaging particles at increasing magnifications (For example, FIG. 4A-4E). In some embodiments, once broken down, the micro- or nano-scale hybrid-scale fiber matrix components maintain the same fiber diameter and pore size specifications as the base graft material sheet.

The graft material can be broken down in a number of different ways, and the particular method is not limiting. For example, the graft material can be ground up into the powder, such as through mechanical grinding or milling. In some embodiments, the material can be frozen, such as by using cryogenic agents like liquid nitrogen, prior to grinding or cryomilling, though in other embodiments the freezing is not used. In some embodiments, cutting or meshing methods can be employed to break down the graft material, including laser cutting or cryocutting among other cutting or meshing methods. Other methods include ultrasonification to breakdown the material into smaller components.

Figure 5A:
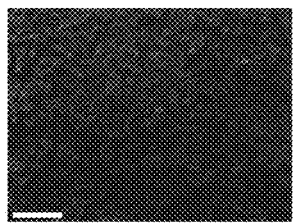
FIGS. 5A-5D illustrates a series of scanning electron micrographs of an embodiment of a non-woven fiber composition of the disclosure. 5A depicts a SEM image of sieving particles less than 150 µm. 5B depicts a SEM image of sieving particles between 150-355 µm. 5C depicts a SEM image of sieving particles greater than 355 µm. 5D depicts a SEM of a homogenous mixture before sieving.
Figure 5B:
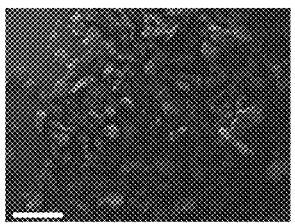
Figure 5C:
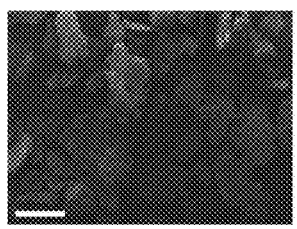
Figure 5D:
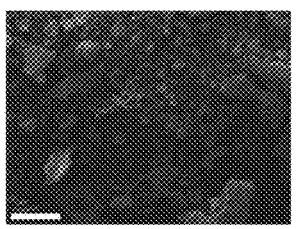

At any time during or after the process of breaking down or otherwise producing micro- or nano-scale, hybrid-scale fiber matrix components, including pre- or post-processing, a number of treatments and processes may be applied to the hybrid-scale fiber matrix components. These include but are not limited to, sieving or particle sorting based on physical characteristics of resultant micro- or nano-scale hybrid-scale fiber matrix components, including surface area, size, shape, mass, density, pourability, deployability, flowability, charge, viscosity, color, or reflectivity. As shown in FIGS. 5A-5D, homogenous mixtures of hybrid-scale fiber matrix components may be separated based on size. FIG. 5A illustrates a SEM image based on sieving of less than 150 μm. FIG. 5B illustrates a SEM image based on sieving of 150-355 μm. FIG. 5C illustrates a SEM image based on sieving of greater than 355 μm. Lastly, FIG. 5D illustrates a SEM image based on a homogenous mixture of particles before sieving. In some embodiments, a post processing step may consist of removing latent electrical charge to achieve an antistatic effect. In some embodiments, moisture changing post-processing treatments may be employed on hybrid-scale fiber matrix components, including nitrogen backfilling. In some embodiments, plasma or other chemical treatments may be utilized to modify resulting surfaces of the hybrid-scale fiber matrix components.

The powder itself can have a D50 diameter of less than 1 mm (or less than about 1 mm). In some embodiments, the D50 of the powder can be around 1 micron (or about 1 micron). In some embodiments, the D50 of the powder can be under 5 mm (5000 µm). In some embodiments, the powder can have a D50 in the range between 1 µm and 2000 µm (or between about 1 µm and about 2000 µm). In some embodiments, the powder can have a D50 in a range between 1 µm and 5000 µm (or between about 1 µm and about 5000 µm). Additionally, in some embodiments, the D50 diameter of the powder can be between 1-100 µm, 30-60 µm, 100-250 µm, 250-500 µm, 500-1000 µm, 1000-2000 µm, or 2000-5000 µm. In some embodiments, the powder can have a d50 of about 1 µm, about 5 µm, about 10 µm, about 100 µm, about 500 µm, about 1000 µm, about 1500 µm, about 2000 µm, about 3000 µm, about 4000 µm, about 5000 µm, and/or comprise d50 values within a range defined by two of the aforementioned values.

Figure 6:
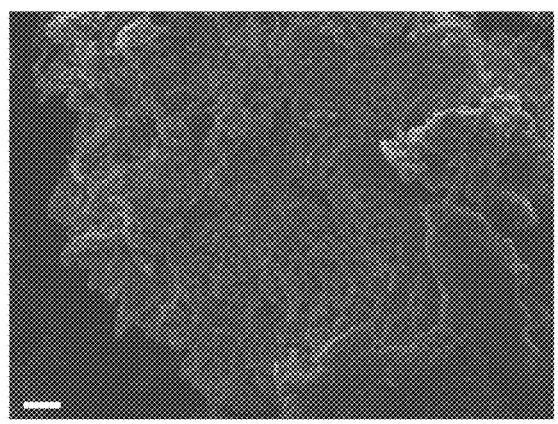
FIG. 6 illustrates a set of scanning electron micrographs of an embodiment of a non-woven fiber composition of the disclosure, illustrating SEM images of fibers fusing together.
Figure 6:
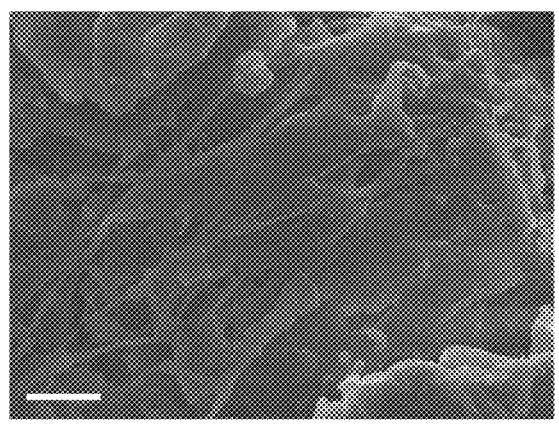

In some embodiments, at least 1, 10, 20, 30, 40, 50, 60, 70, 80, 85, 90, 95, or 99% (or at least about 1, about 10, about 20, about 30, about 40, about 50, about 60, about 70, about 80, about 85, about 90, about 95, or about 99%) of the particles can include the hybrid-scale fiber matrix structure of the original graft material. In some embodiments, fibrous structures inherent in the particles may be mixed or fused with other fibers or nonfibrous structures, as shown in FIG. 6. In some embodiments, mixed or fused fibers may form a solid surface. In some embodiments, all (or about all) of the particles can include the hybrid-scale fiber matrix structure of the original graft material. For example, the particles can include parallel or random fiber orientations, depending on the original structure of the graft material. In some embodiments, hybrid-scale fiber matrix structures are smaller than the overall particle sizes and can be maintained during the creation of the particles. In some embodiments, the hybrid-scale fiber matrix structures are maintained by fiber-fiber interactions.

In some embodiments, the precursors of the graft material can be ground up or milled as discussed above. In some embodiments, particles may be sorted based on physical and mechanical parameters, including but not limited to: surface area, size, shape, mass, density, pourability, deployability, flowability, charge, viscosity, color, or reflectivity.

In some embodiments, the particles can be incorporated into a hydrogel. The hydrogel can be, for example, any crosslinked hydrophilic polymer. In some embodiments, the particles may be mixed with other powder populations consisting of particles with different physical or mechanical properties.

In some embodiments, the particles can be mixed with a fluid to create an injectable solution. The liquid can be, for example, water, phosphate buffer saline, hyaluronic acid, platelet-rich plasma, gels, collagen-based solution, bone marrow aspirate, other chemicals and drugs to enhance injectability and healing response, and combinations thereof. In some embodiments, the particles can be mixed into a solution that allows or encourages interlinking of particles. In some embodiments, the particles do not interlink outside of the natural bodily reformation when the particles are in use.

Tissue Repair

In some embodiments, the present disclosure is directed to a method of tissue repair in an individual in need thereof. The method can include: applying a non-woven graft material to a surgical field, wherein the non-woven graft material comprises a first fiber composition and a second fiber composition. The method can further include: applying a non-woven graft material or a hybrid-scale fiber matrix to a surgical field, wherein the non-woven graft material comprises a first fiber composition and a second fiber composition, wherein the non-woven graft material or a hybrid-scale fiber matrix is packed, spread, or otherwise scattered over a tissue. The method is particularly suitable for repairing tissues such as, for example, dura mater, pericardium, small intestinal submucosa, dermis, epidermis, tendon, trachea, heart valve leaflet, gastrointestinal tract, and cardiac tissue. Suitable tissue repair procedures include, for example, neurosurgeries such as dura mater repair, skin grafts, tracheal repair, gastrointestinal tract repair (e.g., abdominal hernia repair, ulcer repair), cardiac defect repair, head and neck surgeries, application to bone fractures, and burn repair.

Suitably, the non-woven graft material includes a first fiber composition, wherein the first fiber composition includes a polymer selected from polycaprolactone (poly(ε-caprolactone), PCL), polydioxanone (PDO), poly(glycolic acid) (PGA), poly(L-lactic acid) (PLA), poly(lactide-co-glycolide) (PLGA), poly(L-lactide) (PLLA), poly(D,L-lactide) (P(DLLA)), poly(ethylene glycol) (PEG), montmorillonite (MMT), poly(L-lactide-co-ε-caprolactone) (P(LLA-CL)), poly(ε-caprolactone-co-ethyl ethylene phosphate) (P(CL-EEP)), poly[bis(p-methylphenoxy)phosphazene] (PNmPh), poly(3-hydroxybutyrate-co-3-hydroxyvalerate) (PHBV), poly(ester urethane) urea (PEUU), poly(p-dioxanone) (PPDO), polyurethane (PU), polyethylene terephthalate (PET), poly(ethylene-co-vinylacetate) (PEVA), poly(ethylene oxide) (PEO), poly(phosphazene), poly(ethylene-co-vinyl alcohol), polymer nanoclay nanocomposites, poly(ethylenimine), poly(ethyleneoxide), poly vinylpyrrolidone; polystyrene (PS) and combinations thereof. Particularly suitable polymers include poly(lactic-co-glycolic acid), polydioxanone, polycaprolactone, and combinations thereof.

Suitably, the non-woven graft material includes a second fiber composition, wherein the second fiber composition includes a polymer selected from polycaprolactone (poly(ε-caprolactone), PCL), polydioxanone (PDO), poly(glycolic acid) (PGA), poly(L-lactic acid) (PLA), poly(lactide-co-glycolide) (PLGA), poly(L-lactide) (PLLA), poly(D,L-lactide) (P(DLLA)), poly(ethylene glycol) (PEG), montmorillonite (MMT), poly(L-lactide-co-ε-caprolactone) (P(LLA-CL)), poly(ε-caprolactone-co-ethyl ethylene phosphate) (P(CL-EEP)), poly[bis(p-methylphenoxy)phosphazene] (PNmPh), poly(3-hydroxybutyrate-co-3-hydroxyvalerate) (PHBV), poly(ester urethane) urea (PEUU), poly(p-dioxanone) (PPDO), polyurethane (PU), polyethylene terephthalate (PET), poly(ethylene-co-vinylacetate) (PEVA), poly(ethylene oxide) (PEO), poly(phosphazene), poly(ethylene-co-vinyl alcohol), polymer nanoclay nanocomposites, poly(ethylenimine), poly(ethyleneoxide), poly vinylpyrrolidone; polystyrene (PS) and combinations thereof. Particularly suitable polymers include poly(lactic-co-glycolic acid), polydioxanone, polycaprolactone, and combinations thereof.

In a particularly suitable embodiment, the non-woven graft material includes a first fiber composition comprising poly(lactic-co-glycolic acid) and a second fiber composition comprising polydioxanone.

As used herein, "individual in need thereof" refers to an individual having a tissue defect, tissue damage, tissue that is missing due to damage or removal, and tissue damaged by incision. The methods are particularly suitable for use with an individual or subset of individuals having dura defects requiring repair of the dura mater. Individuals having dura defects can be those having a perforation in the dura mater, those having dura mater removed, those having damaged dura mater, and those having dura mater with a surgical incision. The individual in need thereof can be an adult individual, a child, and a pediatric individual. Particularly suitable individuals can be a human. Other particularly suitable individuals can be animals such as primates, pigs, dogs, cats, rabbits, rodents (e.g., mice and rats), and the like.

In some embodiments, the non-woven graft material is secured to the surgical field, such as by suturing the non-woven graft material to the surgical field. In other embodiments, the non-woven graft material is secured to the surgical field, such as by a surgical adhesive. In some embodiments, the non-woven graft material or a hybrid-scale fiber matrix is secured or applied to the surgical field, wherein the non-woven graft material comprises a first fiber composition and a second fiber composition, wherein the non-woven graft material or a hybrid-scale fiber matrix is packed, spread, or otherwise scattered over a tissue. In some embodiments, the non-woven graft material or a hybrid-scale fiber matrix is applied to a wound site, wherein the non-woven graft material or a hybrid-scale fiber matrix is packed, spread, or otherwise scattered over the wound site.

In some embodiments, the powder can be delivered in a variety of forms. These forms are not limiting, but may include delivery as pure powder, mixed in solution, incorporated into a hydrogel, injected by needle, or poured directly on superficial wounds. In some embodiments, multiple powder populations consisting of hybrid-scale fiber matrix components with differing physical, mechanical, or chemical compositions may be combined in varying proportions. In some embodiments, mixtures of multiple powder populations may be administered as described above.

As discussed above, the particles can be used instead of, or in conjunction with, the graft material sheets discussed above. In particular, the particles can be used for skin wound management, such as for wounds which have irregularly shapes that the full sheet graft material would have difficulty covering. Compared to sheets of nanofibers or hybrid-scale fiber matrices, particles of nanofiber or hybrid-scale fiber matrix components may allow for increased conformability and packing of wounds, including irregularly-shaped wounds with hard-to-reach areas and crevices. Additionally, due to a higher surface area-to-volume ratio of individual particles compared to a singular sheet, particles may have an increased ability to absorb moisture and exudates which build up in wounds. In some embodiments, particles may further exhibit high macroscopic porosity to allow for fluid absorption or pass-through. In some embodiments, powders may be injectable or otherwise employed using minimally-invasive techniques. N some embodiments, a plurality of particles can be poured over a wound to fill it partially or completely in, allowing one to "pack" a wound partially or fully with a plurality of particles. In some embodiments, the thickness of one or more layers of particles packed onto a wound may be between 100 μm-1 cm. In some embodiments, the thickness of one or more layers of particles packed onto a wound may be between 100 μm-5 cm. In some embodiments, the thickness of one or more layers of particles packed onto a wound may be between 100 μm-10 cm. In some embodiments, the thickness of one or more layers of particles packed onto a wound may be about 100 μm, about 200 μm, about 300 μm, about 500 μm, about 700 μm, about 1000 μm, about 3000 μm, about 5000 μm, about 7000 μm, about 10,000 μm, about 50,000 μm, about 100,000 μm, and/or may comprise a thickness within a range defined by two of the aforementioned values. Further, embodiments of the particles can be used as soft tissue fillers, such as for plastic and reconstructive surgeries. In some embodiments, the particles can be packed, spread, scattered, sprinkled or poured into a wound.

Advantageously, embodiments of the particles can be used alone, or in combination with other wound therapies, such as wound matrix applications and skin grafting, among others. For example, a layer of particles can be placed in a wound and then a graft attached on top. In some embodiments, the particles can fill in areas that a graft may not cover. In some embodiments, particles may be mixed with other treatment therapies, like bone marrow aspirate or platelet rich plasma, and then applied to the wound. In some embodiments, particles may be combined with other powders, other polymers, drugs, cells, growth factors, or bioactive agents in any proportion.

In some embodiments, the particles can be applied to a suture line, which can help support biological response and accelerate healing.

From the foregoing description, it will be appreciated that inventive nanofiber matrixes and methods of manufacturing and use are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount. Additionally, all values of tables within the disclosure are understood to either be the stated values or, alternatively, about the stated value.

The disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A plurality of particles configured to improve wound healing, the plurality of particles comprising:
    an average diameter of less than 5000 μm;
    wherein the plurality of particles are formed by breaking down a sheet of electrospun graft material, wherein the electrospun graft material possesses a hybrid-scale fiber structure and
    wherein the plurality of particles include the hybrid-scale fiber structure of the electrospun graft material.

2. The plurality of particles of claim 1, wherein plurality of particles are mixed with other fibers or nonfibrous structures.

3. The plurality of particles of claim 1, wherein the sheet of electrospun graft material comprises a plurality of electrospun fibers, the plurality of electrospun fibers formed by electrospinning a first fiber composition and a second fiber composition, the first fiber composition comprising poly (lactic-co-glycolic acid), and the second fiber composition comprising polydioxanone.

4. The plurality of particles of claim 1, wherein the sheet of electrospun graft material comprises a plurality of electrospun fibers, the plurality of electrospun fibers formed by electrospinning a first fiber composition and a second fiber composition, the first fiber composition different from the second fiber composition.

5. The plurality of particles of claim 4,
    wherein the first fiber composition comprises a polymer selected from one or more of: polycaprolactone (poly (ε-caprolactone), PCL), polydioxanone (PDO), poly (glycolic acid) (PGA), poly(L-lactic acid) (PLA), poly (lactide-co-glycolide) (PLGA), poly(L-lactide) (PLLA), poly(D,L-lactide) (P(DLLA)), poly(ethylene glycol) (PEG), montmorillonite (MMT), poly(L-lactide-co-ε-caprolactone) (P(LLA-CL)), poly(ε-caprolactone-co-ethyl ethylene phosphate) (P(CL-EEP)), poly[bis(p-methylphenoxy)phosphazene] (PNmPh), poly(3-hydroxybutyrate-co-3-hydroxyvalerate) (PHBV), poly(ester urethane)urea (PEUU), poly(p-dioxanone) (PPDO), polyurethane (PU), polyethylene terephthalate (PET), poly(ethylene-co-vinylacetate) (PEVA), poly(ethylene oxide) (PEO), poly(phosphazene), poly(ethylene-co-vinyl alcohol), polymer nanoclay nanocomposites, poly(ethylenimine), poly(ethyleneoxide), poly vinylpyrrolidone; polystyrene (PS) and combinations thereof, and;
    wherein the second fiber composition comprises a polymer selected from one or more of: polycaprolactone (poly(ε-caprolactone), PCL), polydioxanone (PDO), poly(glycolic acid) (PGA), poly(L-lactic acid) (PLA), poly(lactide-co-glycolide) (PLGA), poly(L-lactide) (PLLA), poly(D,L-lactide) (P(DLLA)), poly(ethylene glycol) (PEG), montmorillonite (MMT), poly(L-lactide-co-εcaprolactone) (P(LLA-CL)), poly(ε-caprolactone-co-ethyl ethylene phosphate) (P(CL-EEP)), poly[bis(p-methylphenoxy)phosphazene] (PNmPh), poly(3-hydroxybutyrate-co-3-hydroxyvalerate) (PHBV), poly(ester urethane)urea (PEUU), poly(p-dioxanone) (PPDO), polyurethane (PU), polyethylene terephthalate (PET), poly(ethylene-co-vinylacetate) (PEVA), poly(ethylene oxide) (PEO), poly(phosphazene), poly(ethylene-co-vinyl alcohol), polymer nanoclay nanocomposites, poly(ethylenimine), poly(ethyleneoxide), poly vinylpyrrolidone; polystyrene (PS) and combinations thereof.

6. The plurality of particles of claim 1, wherein the plurality of particles are configured to be mixed with fluid to create an injectable solution.

7. The plurality of particles of claim 1, wherein the plurality of particles are sorted based on physical or mechanical properties.

8. The plurality of particles of claim 1, wherein the plurality of particles are sorted based on one or more of: surface area, mass, size, shape, density, pourability, deployability, flowability, charge, viscosity, color, or reflectivity.

9. The plurality of particles of claim 1, wherein the particles are configured to be placed directly onto a wound site.

10. The plurality of particles of claim 1, wherein the particles are incorporated into a hydrogel.

11. The plurality of particles of claim 4, wherein the ratio of the first fiber composition to the second fiber composition can range from about 1:10 to about 10:1.

12. The plurality of particles of claim 1, wherein the particles are further combined with one or more of: bone marrow aspirate, platelet rich plasma, other powders, other polymers, drugs, cells, growth factors, radioactive agents, chemical agents, or bioactive agents.

13. The plurality of particles of claim 11, wherein the plurality of particles are configured to be applied to a suture line.

* * * * *